(12) United States Patent
Xue et al.

US007838676B2

(10) Patent No.: US 7,838,676 B2
(45) Date of Patent: Nov. 23, 2010

(54) BETA-SECRETASE MODULATORS AND METHODS OF USE

(75) Inventors: Qiufen Xue, Newbury Park, CA (US); Brian K. Albrecht, Cambridge, MA (US); Denise Lyn Andersen, Simi Valley, CA (US); Michael Bartberger, Sherman Oaks, CA (US); James Brown, Moorpark, CA (US); Ryan Brown, Belmont, MA (US); Stuart C. Chaffee, Philadelphia, PA (US); Yuan Cheng, Newbury Park, CA (US); Michael Croghan, Thousand Oaks, CA (US); Russell Graceffa, Hampton, NH (US); Scott Harried, Woodland Hills, CA (US); Stephen Hitchcock, Westlake Village, CA (US); Randall Hungate, Camarillo, CA (US); Ted Judd, Simi Valley, CA (US); Matthew Kaller, Ventura, CA (US); Charles Kreiman, Watertown, MA (US); Daniel La, Brookline, MA (US); Patricia Lopez, West Hills, CA (US); Craig Masse, Cambridge, MA (US); Holger Monenschein, Camarillo, CA (US); Thomas Nguyen, Thousand Oaks, CA (US); Thomas Nixey, Newbury Park, CA (US); Vinod F. Patel, Acton, MA (US); Lewis Pennington, Camarillo, CA (US); Matthew Weiss, Boston, MA (US); Bryant Yang, Simi Valley, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 933 days.

(21) Appl. No.: 11/599,901

(22) Filed: Nov. 14, 2006

(65) Prior Publication Data

US 2007/0173521 A1 Jul. 26, 2007

Related U.S. Application Data

(60) Provisional application No. 60/738,766, filed on Nov. 21, 2005.

(51) Int. Cl.
*C07D 498/02* (2006.01)
*C07D 401/00* (2006.01)
(52) U.S. Cl. .......................... 546/18; 546/115
(58) Field of Classification Search .................. 546/18, 546/115
See application file for complete search history.

(56) References Cited

U.S. PATENT DOCUMENTS 5,441,870 A 8/1995 Seubert et al.

| 5,712,130 | A | 1/1998 | Hajko et al. |
| 5,942,400 | A | 8/1999 | Anderson et al. |
| 6,864,290 | B2 | 3/2005 | Schostarez et al. |
| 6,982,264 | B2 | 1/2006 | John et al. |
| 6,992,103 | B2 | 1/2006 | Faller et al. |
| 7,067,542 | B2 | 6/2006 | Schostarez et al. |
| 7,074,799 | B2 | 7/2006 | Bakthavatchalam et al. |
| 7,109,217 | B2 | 9/2006 | Coburn et al. |
| 7,115,652 | B2 | 10/2006 | Yang |
| 7,115,747 | B2 | 10/2006 | Reeder et al. |
| 7,132,568 | B2 | 11/2006 | Yang et al. |
| 7,176,242 | B2 | 2/2007 | John et al. |
| 7,223,774 | B2 | 5/2007 | Aquino et al. |
| 7,244,755 | B2 | 7/2007 | Fisher et al. |
| 7,253,198 | B2 | 8/2007 | Demont et al. |
| 7,291,620 | B2 | 11/2007 | Coburn et al. |
| 7,312,360 | B2 | 12/2007 | TenBrink et al. |
| 7,348,448 | B2 | 3/2008 | Nantermet et al. |
| 7,371,853 | B2 | 5/2008 | Coburn et al. |

(Continued)

FOREIGN PATENT DOCUMENTS

WO 00/17369 A2 3/2000

(Continued)

OTHER PUBLICATIONS

Berge, et al., "Pharmaceutical Salts", J. of Pharmaceutical Sciences, 66(1), 1-19 (1977).

(Continued)

*Primary Examiner*—Janet L. Andres
*Assistant Examiner*—Raymond Covington
(74) *Attorney, Agent, or Firm*—G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

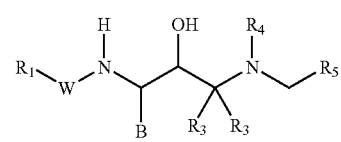

wherein $R^1$, W, B, $R^3$, $R^4$, $R^5$, i and j are defined herein. The invention also comprises pharmaceutical compositions including one or more compounds of Formula I, methods of use for these compounds, including treatment of AD and related diseases, by administering the compound(s) of Formula I, or compositions including them, to a subject. The invention also comprises further embodiments of Formulas II and III, intermediates and processes useful for the preparation of compounds of the invention.

11 Claims, No Drawings

U.S. PATENT DOCUMENTS

| | | |
|---|---|---|
| 2003/0109559 A1 | 6/2003 | Gailunas et al. |
| 2003/0166580 A1 | 9/2003 | Warpehoski et al. |
| 2004/0180939 A1 | 9/2004 | John et al. |
| 2005/0027007 A1 | 2/2005 | Hom |
| 2005/0038019 A1 | 2/2005 | Beck |
| 2005/0054690 A1 | 3/2005 | Aquino et al. |
| 2005/0267199 A1 | 12/2005 | Hom et al. |
| 2006/0211740 A1 | 9/2006 | Demont et al. |
| 2006/0229302 A1 | 10/2006 | Demont et al. |
| 2006/0241133 A1 | 10/2006 | Shearman et al. |
| 2007/0185103 A1 | 8/2007 | Albrecht |
| 2007/0185144 A1 | 8/2007 | Zhong |

FOREIGN PATENT DOCUMENTS

| | | |
|---|---|---|
| WO | 01/70671 A2 | 9/2001 |
| WO | 02/02505 A2 | 1/2002 |
| WO | 03/002518 A1 | 1/2003 |
| WO | 2004/099376 A2 | 11/2004 |
| WO | 2005/058915 A2 | 6/2005 |

OTHER PUBLICATIONS

Citron, M., "β-Secretase Inhibition for the Treatment of Alzheimer's Disease—Promise and Challenge", Trends in Pharmacological Sciences, 25(2), 92-97 (2004).

Ghosh, et al., "Recent Developments of Structure Based β-Secretase Inhibitors for Alzheimer's Disease", Current Topics in Medicinal Chemistry, 5, 1609-1622 (2005).

Joachim, et al., "The Seminal Role of β-Amyloid in the Pathogenesis of Alzheimer Disease", Alzheimer Disease and Associated Disorders, 6(1), 7-34 (1992).

Luo, et al., "Mice deficient in BACE1, the Alzheimer's β-Secretase, have normal Phenotype and Abolished β-Amyloid Generation", Nature Neuroscience, 4(3), 231-232 (2001).

Sabbagh, et al., "β-Amyloid and Treatment Opportunities for Alzheimer's Disease", Alzheimer's Disease Review, 3, 1-19 (1998).

Selcoe, D.M., "The Molecular Pathology of Alzheimer's Disease", Neuron, 6, 487-498 (1991).

Seubert, et al., "Isolation and Quantification of Soluble Alzheimer's β-Peptide from Biological Fluids", Nature, 359, 325-327 (1992).

Sinha, et al., "Purification and Cloning of Amyloid Precursor Protein β-Secretase from Human Brain", Nature, 402, 537-540 (1999).

BETA-SECRETASE MODULATORS AND METHODS OF USE

This application claims the benefit of U.S. Provisional Application No. 60/738,766, filed Nov. 21, 2005, which is hereby incorporated herein by reference in its entirety.

FIELD OF THE INVENTION

The invention relates generally to the field of pharmaceutical agents and, more specifically, to pharmaceutically active compounds, pharmaceutical compositions and methods of use thereof, to treat Beta-Secretase mediated disorders, including Alzheimer's disease and plaque formation related conditions. The invention also relates to intermediates and processes useful in the preparation of such compounds.

BACKGROUND OF THE INVENTION

Alzheimer's disease (AD) is a disease that affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is caused by two major physiological factors in the brain. The first factor, beta amyloid plaque formation, supports the "amyloid cascade hyposthesis" which alleges that AD is caused by the formation of characteristic beta amyloid deposits (commonly referred to as beta amyloid "plaques" or "plaque deposits") in the brain and in cerebral blood vessels (beta amyloid angiopathy). The second factor causing AD is intraneuronal tangles, consisting of an aggregate form of the protein tau. Amyloid plaques are thought to be specific for AD, while intraneuronal tangles are also found in other dementia-inducing disorders. Joachim et al., Alz. Dis. Assoc. Dis., 6:7-34 (1992).

Several lines of evidence indicate that progressive cerebral deposition of beta-amyloid peptide (A-beta) plays a seminal role in the pathogenisis of AD and can precede cognitive symptoms by years or even decades. Selkoe, Neuron, 6:487 (1991). Release of A-beta from neuronal cells grown in culture and the presence of A-beta in cerebrospinal fluid (CSF) of both normal individuals and AD patients has been demonstrated. Seubert et al., Nature, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Herditary Cerebral Hemorrhage with Amyloidosis of the Dutch-type (HCHWA-D), and other neurodegenerative disorders.

It has been hypothesized that A-Beta formation is a causative precursor or factor in the development of AD. Deposition of A-beta in areas of the brain responsible for cognitive factors is a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acids. A-beta 42 (42 amino acids long) is thought to be the major component of these plaque deposits. Citron, Trends in Pharmacological Sciences, 25(2):92-97 (2004).

Several aspartyl proteases are thought to be involved in the processing or cleavage of APP, resulting in the formation of A-beta peptide. Beta secretase (BACE, also commonly referred to as memapsin) is thought to first cleave APP to generate two fragments of the A-beta peptide: (1) a first N-terminus fragment and (2) a second C-99 fragment, which is subsequently cleaved by gamma secretase to generate the C-terminus fragment of the A-beta peptide. APP has also found to be cleaved by alpha-secretase to produce alpha-sAPP, a secreted form of APP that does not result in beta-amyloid plaque formation. This alternate pathway precludes the formation of A-beta peptide. A decription of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., Nature, 402:537-554 (1999), (p510) and PCT application WO 2000/17369. It has been proposed that A-beta peptide accumulates as a result of APP processing by BACE. Moreoevr, in vivo processing of APP at the beta secretase cleavage site is thought to be a rate-limiting step in A-beta production. Sabbagh, M. et al., Alz. Dis. Rev., 3:1-19 (1997). Thus, inhibition of the BACE enzyme activity is desirable for the treatment of AD.

Studies have shown that the inhibition of BACE may be linked to the treatment of AD. BACE 1 knockout mice fail to produce A-beta, and present a normal phenotype. When crossed with transgenic mice that over express APP, the progeny show reduced amounts of A-beta in brain extracts as compares with control animals (Luo et al., Nature Neuroscience, 4:231-232 (2001)). This evidence further supports the concept that inhibition of beta secretase activity and a corresponding reduction of A-beta in the brain should provide a therapeutic method for treating AD and other beta amyloid or plaque related disorders.

Several approaches have been taken to treat AD and plaque-related disorders. One approach has been to reduce the formation of plaque on the brain. Particularly, a common approach has been to inhibit the activity of beta secretase. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, Wo 04/094384, Wo 04/094413, WO 03/006423, WO 03/050073, WO 03/029169 and WO 04/000821, describe inhibitors of beta secretase, useful for treating AD and other beta-secretase mediated disorders.

BRIEF DESCRIPTION OF THE INVENTION

The present invention provides a new class of compounds useful for the modulation of beta secretase and, to that end, useful for the regulation or reduction of the formation of A-beta peptide and, consequently, the reduction of beta amyloid plaque formation on the brain. Accordingly, the compounds of the invention are useful for the treatment of Alzheimer's disease and other beta secretase mediated disorders.

The compounds provided by the invention, including stereoisomers, tautomers, solvates, pharmaceutically acceptable salts, derivatives or prodrugs thereof, are defined by general Formula I

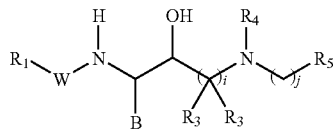

I wherein B, W, $R^1$, $R^3$, $R^4$, $R^5$, i and j are as described below. The invention also provides procedures for making compounds of Formula I, as well as intermediates useful in such procedures.

The compounds provided by the invention are capable of modulating beta secretase. To this end, the invention further provides for the use of these compounds for therapeutic, prophylactic, acute and/or chronic treatment of beta secretase mediated diseases, such as those described herein. For example, the compounds are useful for the prophylaxis and treatment of AD and other diseases or conditions involving amyloid plaque formation on the brain.

The invention also provides pharmaceutical compositions, which comprise one or more compounds of the invention, methods for the treatment of beta secretase mediated diseases, such as AD, using the compounds and compositions of the invention, and intermediates and processes useful for the preparation of the compounds of the invention. The invention also provides the preparation of a a pharmaceutical composition or of a medicament, containing one or more of the compounds, useful to attenuate, alleviate, or treat disorders through inhibition of beta secretase. For example, and in one embodiment, the invention provides a pharmaceutical composition comprising an effective dosage amount of a compound of Formula I in association with at least one pharmaceutically acceptable carrier.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by

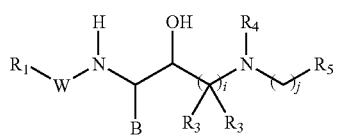

I wherein $R^1$ is a fully unsaturated 5-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—$(CR^{2a}R^{2a})_h$—, $R^2$—O—$(CR^{2a}R^{2a})_h$—, $R^2$—S—$(CR^{2a}R^{2a})_h$— or $R^2$—N($R^{2a}$)—$(CR^{2a}R^{2a})_h$—, wherein $R^2$ is $C_1$-$C_{10}$ alkyl, $C_1$-$C_{10}$ alkenyl, $C_1$-$C_{10}$ alkynyl, $C_1$-$C_{10}$ haloalkyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H, OH, $NO_2$, CN, $NH_2$, halo, $C_1$-$C_{10}$ alkyl, $C_1$-$C_{10}$ alkoxyl or haloalkyl; and h is 0, 1, 2 or 3;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is 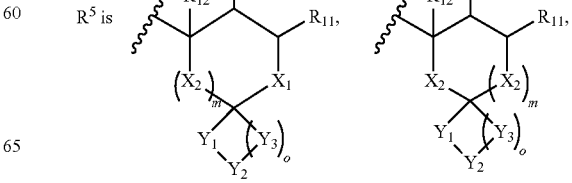

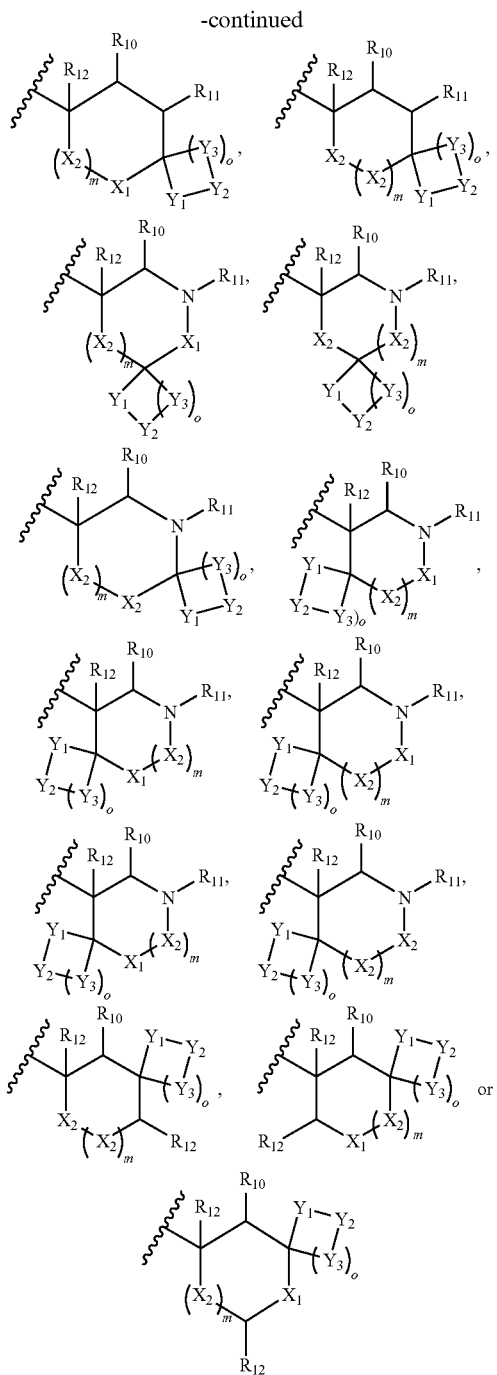

wherein $X^1$ is $C(=O)$, O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than two of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$- alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

alternatively, R$^{10}$ and R$^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of R$^{12}$, R$^{13}$, R$^{14}$ or R$^{15}$ and optionally fused to a 4-7 membered third ring, the third ring formed of carbon atoms optionally including 1-3 heteroatoms selected from O, N, or S, and optionally substituted independently with 1-5 substituents of R$^{12}$, R$^{13}$, R$^{14}$ or R$^{15}$;

R$^{12}$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl, phenyl or R$^{14}$;

R$^{13}$ is NR$^{14}$R$^{15}$, NR$^{15}$R$^{15}$, OR$^{14}$, SR$^{14}$, OR$^{15}$, SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{14}$C(O)R$^{14}$, NR$^{14}$C(O)R$^{15}$, NR$^{15}$C(O)R$^{14}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^{15}$; and R$^{15}$ is H, halo, haloalkyl, CN, OH, NO$_2$, NH$_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, C$_{1-10}$-alkylamino-, C$_{1-10}$-dialkylamino-, C$_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, Formula I includes compounds wherein R$^1$ is an optionally substituted phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl or benzotriazolyl, in conjunction with any of the above or below embodiments.

In another embodiment, Formula I includes compounds wherein R$^1$ is

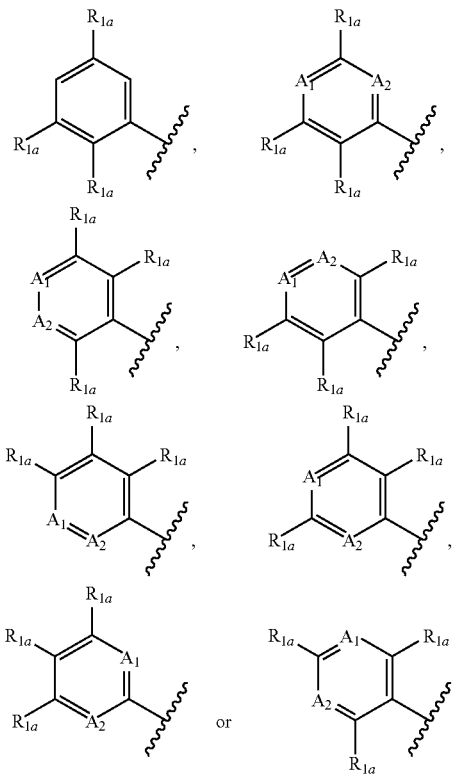

wherein
one of A$^1$ and A$^2$ is N and the other of A$^1$ and A$^2$ is CR$^{1a}$ or each of A$^1$ and A$^2$, independently, is N;

each R$^{1a}$, independently, is R$^7$, R$^8$, R$^9$, C(O)R$^7$, C(O)R$^8$, C(O)NR$^7$R$^7$, C(S)NR$^7$R$^7$, C(O)NR$^7$R$^8$, C(S)NR$^7$R$^8$, S(O)$_2$NR$^7$R$^7$, S(O)$_2$R$^8$, or S(O)$_2$NR$^7$R$^8$;

alternatively, two adjacent R$^{1a}$'s taken together with the carbon atoms to which they are attached form a partially or fully saturated or unsaturated 3-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S and optionally substituted independently with one or more substituents of oxo, R$^7$, R$^8$, R$^9$, NR$^7$R$^7$, NR$^7$R$^8$, OR$^7$, SR$^7$, OR$^8$, SR$^8$, C(O)R$^7$, OC(O)R$^7$, COOR$^7$, C(O)R$^8$, OC(O)

$R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^{78}$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$, in conjunction with any of the above or below embodiments.

In another embodiment, the compounds of immediately preceeding embodiment include compounds wherein at least one $R^{1a}$ substituent is an optionally substituted phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxo-pyrrolidinyl, oxo-imidazolidinyl, oxazolinyl, isoxazolinyl, thiazolinyl, pyrazolinyl, morpholinyl, piperidinyl, piperazinyl, pyranyl, oxo-pyranyl, dioxozinyl, cyclopropyl, cyclobutyl, cyclopentyl, cyclohexyl or cycloheptyl ring, in conjunction with any of the above or below embodiments.

In another embodiment, Formula I includes compounds wherein W is —C(=O)—, in conjunction with any of the above or below embodiments.

In another embodiment, Formula I includes compounds wherein W is —OC(=O)—, in conjunction with any of the above or below embodiments.

In another embodiment, Formula I includes compounds wherein W is —NHC(=O)—, in conjunction with any of the above or below embodiments.

In another embodiment, Formula I includes compounds wherein W is —S(=O)$_b$— wherein b is 1 or 2, in conjunction with any of the above or below embodiments.

In another embodiment, Formula I includes compounds wherein W is —NHS(=O)$_b$— wherein b is 1 or 2, in conjunction with any of the above or below embodiments.

In another embodiment, Formula I includes compounds wherein B is $R^2$—$(CR^{2a}R^{2a})_h$— wherein each $R^{2a}$, independently, is H, OH, NO$_2$, CN, NH$_2$, C$_1$-C$_{10}$ alkyl, C$_1$-C$_{10}$ alkoxyl or haloalkyl, in conjunction with any of the above or below embodiments.

In another embodiment, Formula I includes compounds wherein B is $R^2$—O—$(CR^{2a}R^{2a})_h$— wherein each $R^{2a}$, independently, is H, OH, NO$_2$, CN, NH$_2$, C$_1$-C$_{10}$ alkyl, C$_1$-C$_{10}$ alkoxyl or haloalkyl, in conjunction with any of the above or below embodiments.

In another embodiment, Formula I includes compounds wherein B is $R^2$—S—$(CR^{2a}R^{2a})_h$— wherein each $R^{2a}$, independently, is H, OH, NO$_2$, CN, NH$_2$, C$_1$-C$_{10}$ alkyl, C$_1$-C$_{10}$ alkoxyl or haloalkyl, in conjunction with any of the above or below embodiments.

In another embodiment, Formula I includes compounds wherein B is $R^2$—N($R^{2a}$)—$(CR^{2a}R^{2a})_h$— wherein each $R^{2a}$, independently, is H, OH, NO$_2$, CN, NH$_2$, C$_1$-C$_{10}$ alkyl, C$_1$-C$_{10}$ alkoxyl or haloalkyl, in conjunction with any of the above or below embodiments.

In another embodiment, Formula I includes compounds wherein B is $R^2$—$(CHR^{2a})_h$— wherein $R^{2a}$ is OH, NO$_2$, CN, NH$_2$, C$_1$-C$_{10}$ alkyl, C$_1$-C$_{10}$ alkoxyl or haloalkyl, in conjunction with any of the above or below embodiments.

In another embodiment, Formula I includes compounds wherein B is $R^2$—$(CH_2)_h$—, in conjunction with any of the above or below embodiments.

In another embodiment, Formula I includes compounds wherein B is $R^2$—O—$(CH_2)_h$—, in conjunction with any of the above or below embodiments.

In another embodiment, Formula I includes compounds wherein B is $R^2$—S—$(CH_2)_h$—, in conjunction with any of the above or below embodiments.

In another embodiment, Formula I includes compounds wherein B is $R^2$—NH—$(CH_2)_h$—, in conjunction with any of the above or below embodiments.

In another embodiment, Formula I includes compounds wherein $R^2$ is an optionally substituted ring system selected from phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, in conjunction with any of the above or below embodiments.

In another embodiment, Formula I includes compounds wherein $R^2$ is an optionally substituted ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl and benzimidazoly as $R^2$, in conjunction with any of the above or below embodiments.

In another embodiment, Formula I includes compounds wherein $R^2$ is C$_1$-C$_{10}$ alkyl, C$_1$-C$_{10}$ alkenyl or C$_1$-C$_{10}$ alkynyl, in conjunction with any of the above or below embodiments.

In another embodiment, Formula I includes compounds wherein $R^2$ is C$_1$-C$_{10}$ haloalkyl, in conjunction with any of the above or below embodiments.

In another embodiment, Formula I includes compounds wherein each $R^3$, independently, is H, haloalkyl, CN, C$_{1-10}$-alkyl or C$_{3-10}$-cycloalkyl, in conjunction with any of the above or below embodiments.

In another embodiment, Formula I includes compounds wherein each $R^3$, independently, is H, CF$_3$, CN, CH$_3$ or C$_2$H$_5$, in conjunction with any of the above or below embodiments.

In another embodiment, Formula I includes compounds wherein $R^3$ is H, in conjunction with any of the above or below embodiments.

In another embodiment, Formula I includes compounds wherein $R^3$ is C$_{1-10}$-alkyl, in conjunction with any of the above or below embodiments.

In another embodiment, Formula I includes compounds wherein $R^4$ is H, haloalkyl, CN, C$_{1-10}$-alkyl or C$_{3-10}$-cycloalkyl, in conjunction with any of the above or below embodiments.

In another embodiment, Formula I includes compounds wherein $R^4$ is H, CN or C$_{1-10}$-alkyl, in conjunction with any of the above or below embodiments.

In another embodiment, Formula I includes compounds wherein $R^4$ is H, in conjunction with any of the above or below embodiments.

In another embodiment, Formula I includes compounds wherein $R^4$ is C$_{1-10}$-alkyl, in conjunction with any of the above or below embodiments.

In another embodiment, Formula I includes compounds as wherein each $R^3$, independently, is H, haloalkyl, CN, C$_{1-10}$- alkyl, $C_{2-10}$-alkenyl or $C_{2-10}$-alkynyl; and $R^4$ is H or $C_{1-10}$-alkyl, in conjunction with any of the above or below embodiments.

In another embodiment, Formula I includes compounds wherein h is 1, in conjunction with any of the above or below embodiments.

In another embodiment, Formula I includes compounds wherein h is 2, in conjunction with any of the above or below embodiments.

In another embodiment, Formula I includes compounds wherein i is 1, in conjunction with any of the above or below embodiments.

In another embodiment, Formula I includes compounds wherein i is 2, in conjunction with any of the above or below embodiments.

In another embodiment, Formula I includes compounds wherein i is 3, in conjunction with any of the above or below embodiments.

In another embodiment, Formula I includes compounds wherein j is 0, in conjunction with any of the above or below embodiments.

In another embodiment, Formula I includes compounds wherein j is 1, in conjunction with any of the above or below embodiments.

In another embodiment, Formula I includes compounds wherein j is 2, in conjunction with any of the above or below embodiments.

In another embodiment, Formula I includes compounds wherein h is 1, i is 1, and j is 0, in conjunction with any of the above or below embodiments.

In another embodiment, Formula I includes compounds wherein $R^5$ is

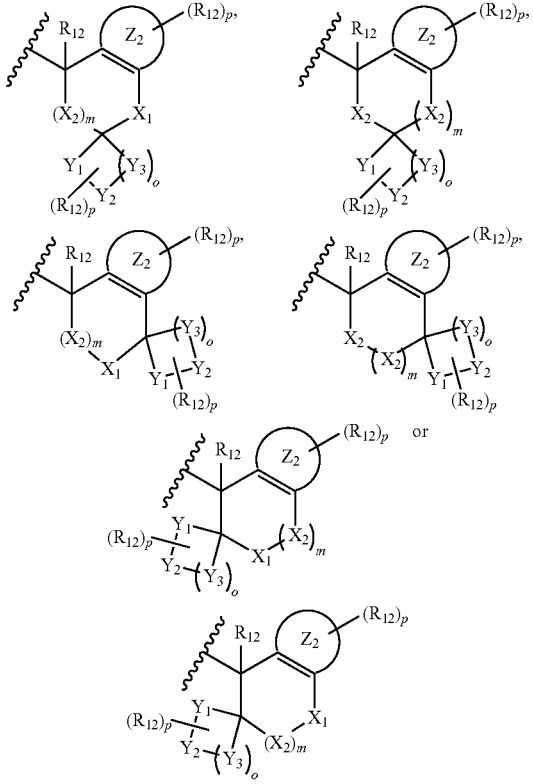

wherein m, o, $R^{12}$, $X^1$, $X^2$, $Y^1$, $Y^2$ and $Y^3$ are as defined hereinabove for formula I;

$Z^2$ is an optionally substituted, partially saturated or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than one of $Y^1$, $Y^2$ and $Y^3$ is O, S or $NR^{12}$ and (b) when o is 0, then each of $Y^1$ and $y^2$ is $CR^{12}R^{12}$; and p is 0, 1, 2, 3, 4 or 5, in conjunction with any of the above or below embodiments.

In the immediately preceeding embodiment, Formula I includes compounds wherein $Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring, in conjunction with any of the above or below embodiments.

In the preceeding embodiment of $R^5$ above, the compounds of Formula I include $CR^{12}R^{12}$ as $X^1$, in conjunction with any of the above or below embodiments.

In the preceeding embodiment of $R^5$ above, the compounds of Formula I include $CHR^{12}$ as $X^1$, in conjunction with any of the above or below embodiments.

In the preceeding embodiment of $R^5$ above, the compounds of Formula I include $CH_2$ as $X^1$, in conjunction with any of the above or below embodiments.

In the preceeding embodiment of $R^5$ above, the compounds of Formula I include C(=O) as $X^1$, in conjunction with any of the above or below embodiments.

In the preceeding embodiment of $R^5$ above, the compounds of Formula I include O as $X^1$, in conjunction with any of the above or below embodiments.

In the preceeding embodiment of $R^5$ above, the compounds of Formula I include S as $X^1$, in conjunction with any of the above or below embodiments.

In the preceeding embodiment of $R^5$ above, the compounds of Formula I include $NR^{12}$ as $X^1$, in conjunction with any of the above or below embodiments.

In the preceeding embodiment of $R^5$ above, the compounds of Formula I include NH as $X^1$, in conjunction with any of the above or below embodiments.

In the preceeding embodiment of $R^5$ above, the compounds of Formula I include $CR^{12}R^{12}$ as each $X^2$, independently, in conjunction with any of the above or below embodiments.

In the preceeding embodiment of $R^5$ above, the compounds of Formula I include $CHR^{12}$ as each $X^2$, independently, in conjunction with any of the above or below embodiments.

In the preceeding embodiment of $R^5$ above, the compounds of Formula I include $CH_2$ as each $X^2$, independently, in conjunction with any of the above or below embodiments.

In the preceeding embodiment of $R^5$ above, the compounds of Formula I include $CR^{12}R^{12}$ as each of $Y^1$, $Y^2$ and $Y^3$, independently, in conjunction with any of the above or below embodiments.

In the preceeding embodiment of $R^5$ above, the compounds of Formula I include $CHR^{12}$ as each of $Y^1$, $Y^2$ and $Y^3$, independently, in conjunction with any of the above or below embodiments.

In the preceeding embodiment of $R^5$ above, the compounds of Formula I include $CH_2$ as each of $Y^1$, $Y^2$ and $Y^3$, independently, in conjunction with any of the above or below embodiments.

In the preceeding embodiment of $R^5$ above, the compounds of Formula I include O as any one or two of $Y^1$, $Y^2$ and $Y^3$, independently, in conjunction with any of the above or below embodiments.

In the preceeding embodiment of $R^5$ above, the compounds of Formula I include S as any one or two of $Y^1$, $Y^2$ and $Y^3$, independently, in conjunction with any of the above or below embodiments.

In the preceeding embodiment of $R^5$ above, the compounds of Formula I include $NR^{12}$ as any one or two of $Y^1$, $Y^2$ and $Y^3$, independently, in conjunction with any of the above or below embodiments.

In the preceeding embodiment of $R^5$ above, the compounds of Formula I include O as $Y^2$ and $CH_2$ as each of $Y^1$ and $Y^3$, in conjunction with any of the above or below embodiments.

In the preceeding embodiment of $R^5$ above, the compounds of Formula I include S as $Y^2$ and $CH_2$ as each of $Y^1$, and $Y^3$, in conjunction with any of the above or below embodiments.

In the preceeding embodiment of $R^5$ above, the compounds of Formula I include $NR^{12}$ as $Y^2$ and $CH_2$ as each of $Y^{1, and\ Y3}$, in conjunction with any of the above or below embodiments.

In another embodiment, the compounds of Formula I include as $R^5$

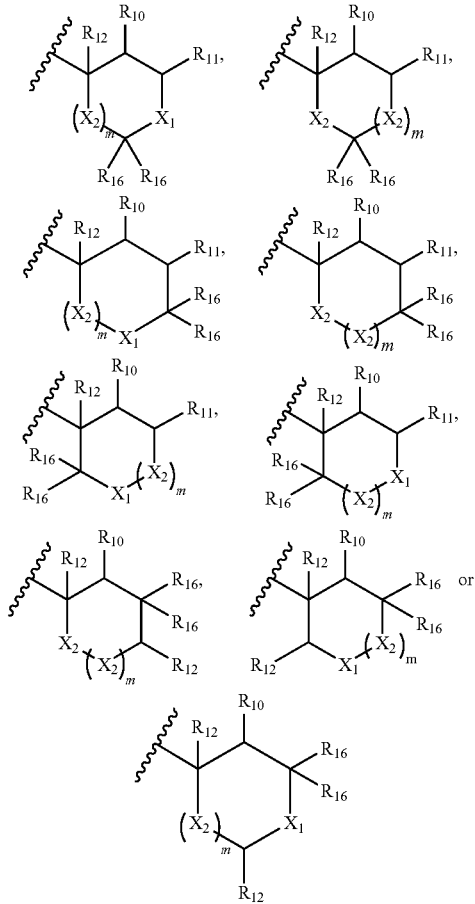

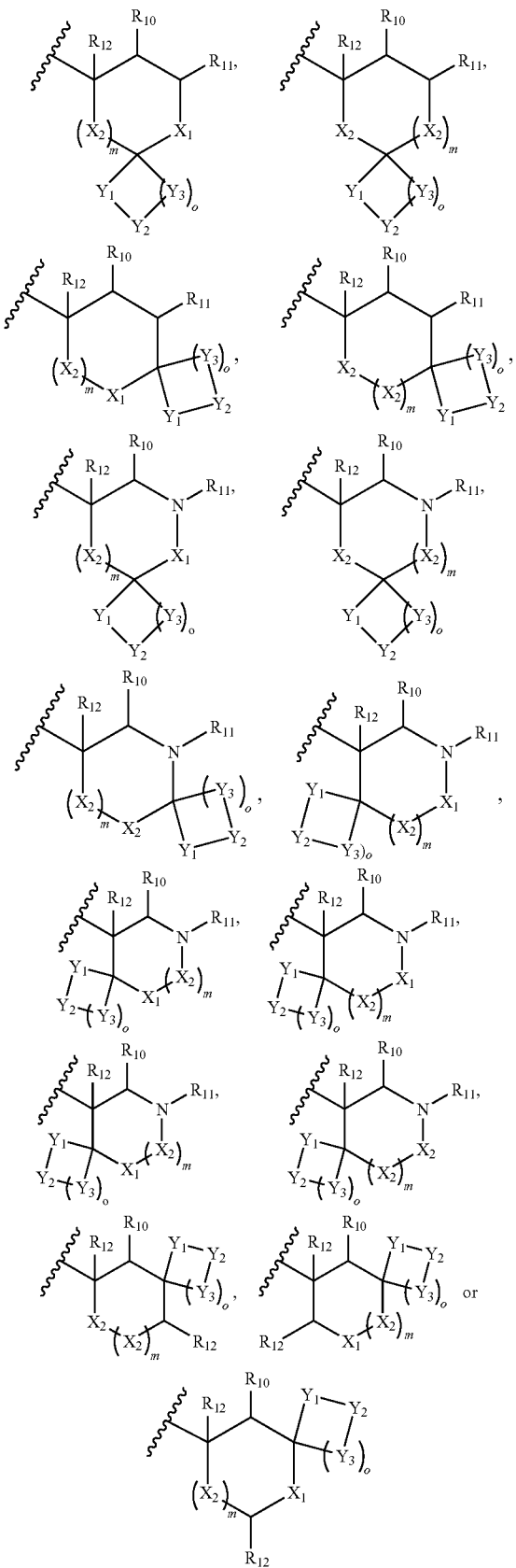

wherein $X^1$ is C(=O), O, S or $NR^{12}$;
each $X^2$, independently, is $CR^{12}R^{12}$;
m is 0, 1 or 2; and
each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl, in conjunction with any of the above or below embodiments.

In another embodiment, the compounds of Formula I include as $R^5$ wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;

m is, 0, 1 or 2; and o is 0, 1, 2, 3, 4 or 5;

provided that (a) no more than two of $Y^1$, $Y^2$ and $Y^3$ is O, S or $NR^{12}$ and (b) when o is 0, then each of $Y^1$ and $Y^2$ is $CR^{12}R^{12}$, in conjunction with any of the above or below embodiments.

In another embodiment, the compounds of Formula I include as $R^5$

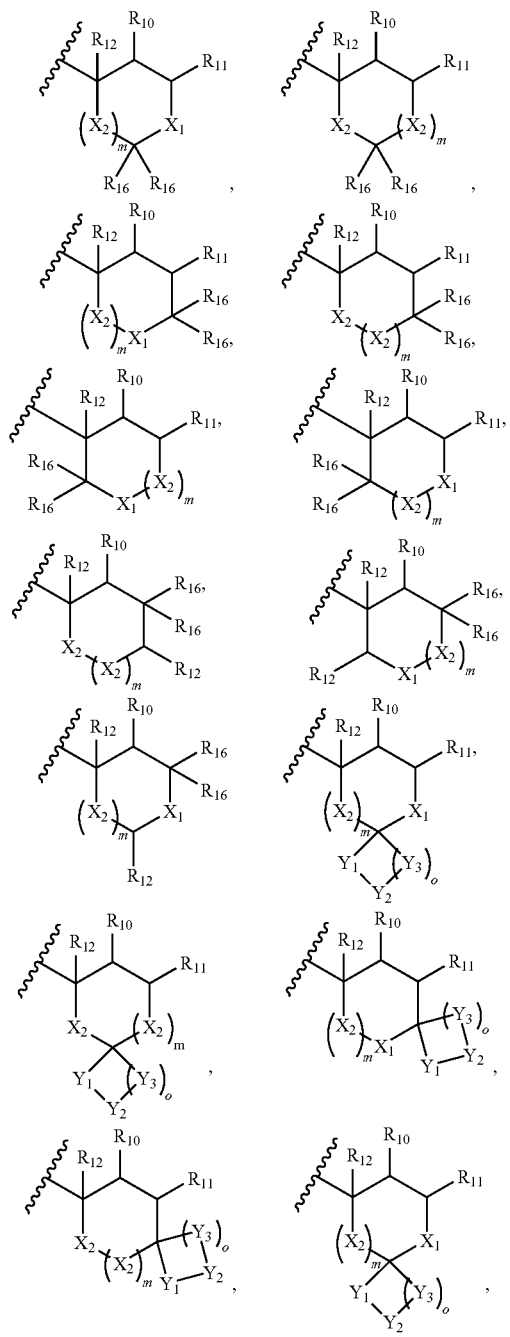

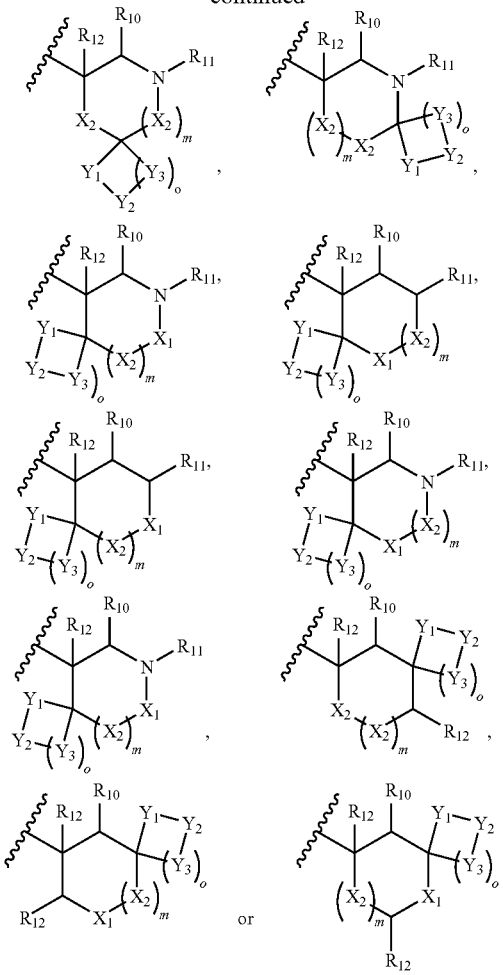

wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;

m is 0, 1 or 2; and o is 0, 1, 2, 3, 4 or 5;

provided that (a) no more than two of $Y^1$, $Y^2$ and $Y^3$ is O, S or $NR^{12}$ and (b) when o is 0, then each of $Y^1$ and $Y^2$ is $CR^{12}R^{12}$, in conjunction with any of the above or below embodiments.

In another embodiment, the compounds of Formula I include compounds wherein $R^5$ is

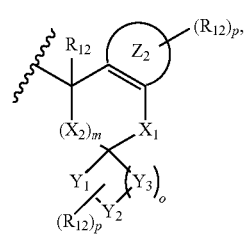

wherein m, o, $X^1$, $X^2$, $Y^1$, $Y^2$ and $Y^3$ are as defined herein with respect to compounds of formula I, $Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring, each p, independently, is 0, 1, 2, 3, 4 or 5, and $R^{12}$, in each instance, is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$, in conjunction with any of the above or below embodiments.

In another embodiment, the compounds of Formula I

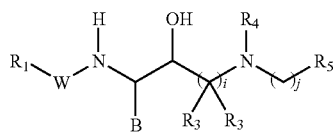

I or stereoisomer, tautomer, solvate, pharmaceutically acceptable salt, derivative or prodrug thereof, include compounds wherein $R^1$ is a fully unsaturated 5-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said beteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—O—$(CR^{2a}R^{2a})_h$—, $R^2$—S—$(CR^{2a}R^{2a})_h$— or $R^2$—N($R^{2a}$)—$(CR^{2a}R^{2a})_h$—, wherein $R^2$ is $C_1$-$C_{10}$ alkyl, $C_1$-$C_{10}$ alkenyl, $C_1$-$C_{10}$ alkynyl, $C_1$-$C_{10}$ haloalkyl, or a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C$ $(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1 or 2;

i is 1, 2 or 3;

j is 0, 1 or 2;

each $R^3$, independently, is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

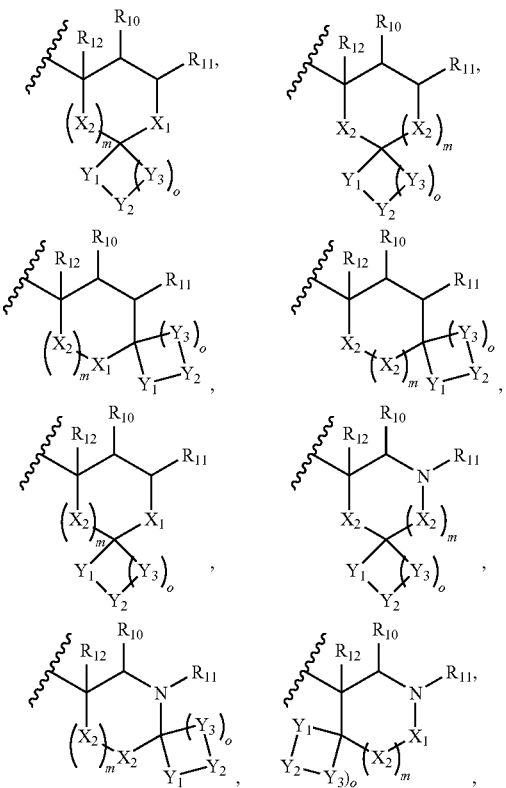

-continued

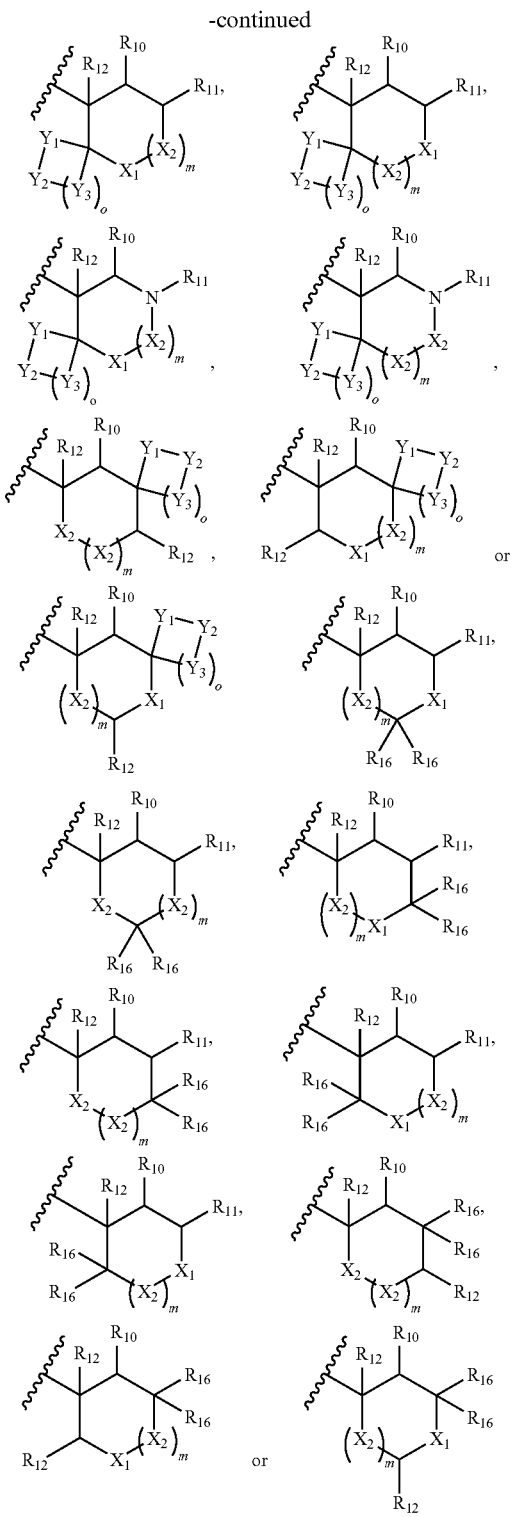

wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;

provided that (a) no more than one of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $N^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutyl, tert-butoxyl, isobutyl, sec-butyl, tert-butyl, cyclobutyl, pentyl, cyclopentyl, hexyl, cyclohexyl, benzyl or phenyl; and each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl.

In another embodiment, the invention provides compounds of Formula II,

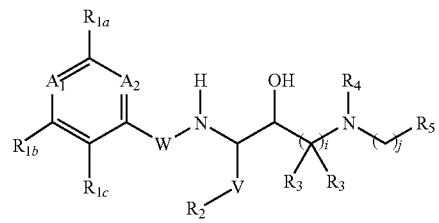

II or stereoisomer, tautomer, solvate, pharmaceutically acceptable salt, derivative or prodrug thereof, wherein $A^1$ is N or $CR^{1a}$;

$A^2$ is N or $CR^{1c}$;

each $R^{1a}$, independently, is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;

$R^{1b}$ is $R^7$, $R^8$, $R^9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;

each $R^{1c}$, independently, is H, haloalkyl, halo, CN, $C_{1-10}$-alkyl, $C_{2-10}$-alkenyl or $C_{2-10}$-alkynyl;

W is —C(=O)—, —OC(=O)—, —NHC(=O)—, —S(=O)$_b$— or —NHS(=O)$_b$—, wherein b is 1 or 2;

V is —$(CR^{2a}R^{2a})_h$—, —O—$(CR^{2a}R^{2a})_h$—, —S—$(CR^{2a}R^{2a})_h$— or —$NR^{2a}$—$(CR^{2a}R^{2a})_h$—, wherein each $R^{2a}$, independently, is H $C_1$-$C_{10}$ alkyl or haloalkyl, and h is 0, 1 or 2;

$R^2$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^3$ is H, haloalkyl, CN, $C_{1-10}$-alkyl, $C_{2-10}$-alkenyl or $C_{2-10}$-alkynyl;

$R^4$ is H, haloalkyl, CN, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^8$ or $R^9$;

$R^5$ is

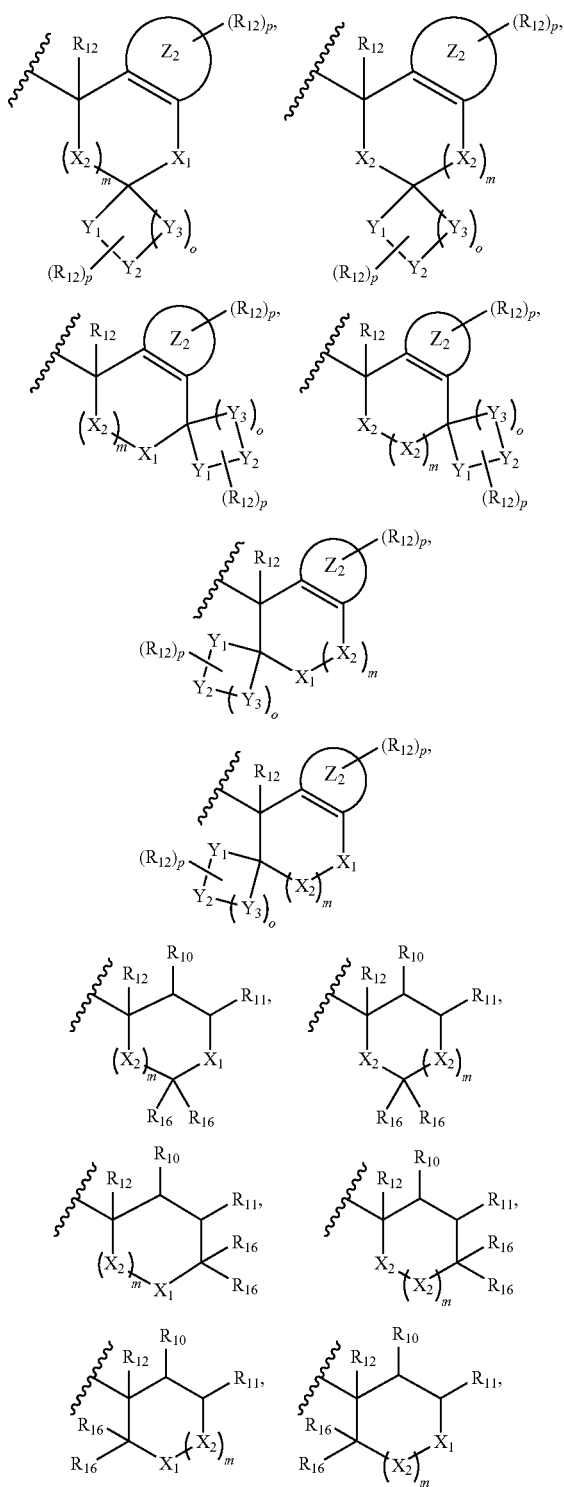

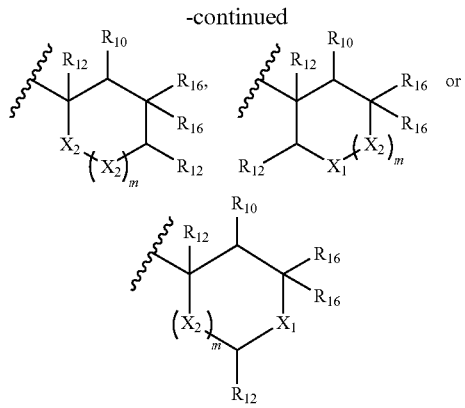

wherein m, o, $R^{12}$, $X^1$, $X^2$, $Y^1$, $Y^2$ and $Y^3$ are as defined in claim 1;

$Z^2$ is an optionally substituted, partially saturated or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than one of $Y^1$, $Y^2$ and $Y^3$ is O, S or $NR^{12}$ and
(b) when o is 0, then each of $Y^1$ and $Y^2$ is $CR^{12}R^{12}$; and p is 0, 1, 2, 3, 4 or 5;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1\text{-}10}$-alkylamino-, $C_{1\text{-}10}$-dialkylamino-, $C_{1\text{-}10}$-thioalkoxyl, benzyl or phenyl;

$R^{10}$ is H, halo, haloalkyl, CN, OH, $NO_2$, $NH_2$, acetyl, $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1\text{-}10}$-alkylamino-, $C_{1\text{-}10}$-dialkylamino-, $C_{1\text{-}10}$-thioalkoxyl, benzyl or phenyl;

$R^{11}$ is H, halo, haloalkyl, CN, OH, $NO_2$, $NH_2$, acetyl, $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1\text{-}10}$-alkylamino-, $C_{1\text{-}10}$-dialkylamino-, $C_{1\text{-}10}$-thioalkoxyl, benzyl or phenyl;

alternatively, $R^{10}$ and $R^{11}$ taken together with the carbon atoms to which they are attached form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1\text{-}10}$-alkylamino-, $C_{1\text{-}10}$-dialkylamino-, $C_{1\text{-}10}$-thioalkoxyl, benzyl or phenyl;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, cyclopropyl, butyl, isobutyl, tert-butyl, cyclobutyl, $C_{1\text{-}10}$-alkylamino-, $C_{1\text{-}10}$-dialkylamino-, $C_{1\text{-}10}$-thioalkoxyl, benzyl, phenyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, tert-butyl, cyclobutyl, $C_{1\text{-}10}$-alkylamino-, $C_{1\text{-}10}$-dialkylamino-, $C_{1\text{-}10}$-thioalkoxyl, benzyl or phenyl;

each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl;

h is 0, 1 or 2;

i is 1, 2 or 3; and j is 0, 1 or 2.

In another embodiment, the compounds of Formula II include O as $X^1$, in conjunction with any of the above or below embodiments.

In another embodiment, the compounds of Formula II include S as $X^1$, in conjunction with any of the above or below embodiments.

In another embodiment, the compounds of Formula II include $NR^{12}$ as $X^1$, in conjunction with any of the above or below embodiments.

In another embodiment, the compounds of Formula II include methyl, ethyl, propyl, isopropyl, butyl, isobutyl or sec-butyl as $R^{16}$, independently, in conjunction with any of the above or below embodiments.

In another embodiment, the compounds of Formula II include each independent embodiment, as described herein for variables A, B, $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, W, V, $X^1$, $X^2$, $Y^1$, $Y^2$, $Y^3$, $Z^1$ and $Z^2$ for compounds of Formula I, independently, in conjunction with any of the above or below embodiments for compounds of Formula II.

In yet another embodiment, the invention provides compounds generally defined by Formula III, A compound of Formula III:

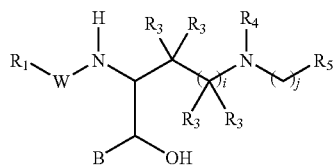

or stereoisomer, tautomer, solvate, pharmaceutically acceptable salt, derivative or prodrug thereof, wherein $R^1$ is a fully unsaturated 5-8 membered monocyclic, 6-12 membered bicyclic, or 7-14 membered tricyclic ring system, said ring system formed of carbon atoms and optionally including 1-3 heteroatoms if monocyclic, 1-6 heteroatoms if bicyclic, or 1-9 heteroatoms if tricyclic, said heteroatoms selected from O, N, or S, wherein said ring system is optionally substituted independently with one or more substituents of oxo, $R^1$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—$(CR^{2a}R^{2a})_h$—, $R^2$—O—$(CR^{2a}R^{2a})_h$—, $R^2$—S—$(CR^{2a}R^{2a})_h$— or $R^2$—$NR^{2a}$—$(CR^{2a}R^{2a})_h$—, wherein $R^2$ is $C_1$-$C_{10}$ alkyl, $C_1$-$C_{10}$ alkenyl, $C_1$-$C_{10}$ alkynyl, $C_1$-$C_{10}$ haloalkyl or a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said $C_1$-$C_{10}$ alkyl, $C_1$-$C_{10}$ alkenyl, $C_1$-$C_{10}$ alkynyl is optionally substituted independently with one or more substituents of $R^9$, and said ring system is optionally substituted independently with one or more substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

each $R^{2a}$, independently, is H, OH, $NO_2$, CN, $NH_2$, $C_1$-$C_{10}$ alkyl, $C_1$-$C_{10}$ alkoxyl or haloalkyl; and h is 0, 1 or 2;

i is 1, 2 or 3;

j is 0, 1 or 2;

each $R^3$, independently, is H, haloalkyl, CN, $C_{1\text{-}10}$-alkyl, $C_{2\text{-}10}$-alkenyl, $C_{2\text{-}10}$-alkynyl, $C_{3\text{-}10}$-cycloalkyl or $C_{4\text{-}10}$-cycloalkenyl, each of the $C_{1\text{-}10}$-alkyl, $C_{2\text{-}10}$-alkenyl, $C_{2\text{-}10}$-alkynyl, $C_{3\text{-}10}$-cycloalkyl and $C_{4\text{-}10}$-cycloalkenyl optionally comprising 1-4 heteroatoms selected from N, O and S and optionally substituted with 1-5 substituents of $R^8$ or $R^9$;

$R^4$ is H, haloalkyl, CN, $C_{1\text{-}10}$-alkyl, $C_{2\text{-}10}$-alkenyl, $C_{2\text{-}10}$-alkynyl, $C_{3\text{-}10}$-cycloalkyl or $C_{4\text{-}10}$-cycloalkenyl, each of the $C_{1\text{-}10}$-alkyl, $C_{2\text{-}10}$-alkenyl, $C_{2\text{-}10}$-alkynyl, $C_{3\text{-}10}$-cycloalkyl and $C_{4\text{-}10}$-cycloalkenyl optionally comprising 1-4 heteroatoms selected from N, O and S and optionally substituted with 1-5 substituents of $R^8$ or $R^9$;

$R^5$ is

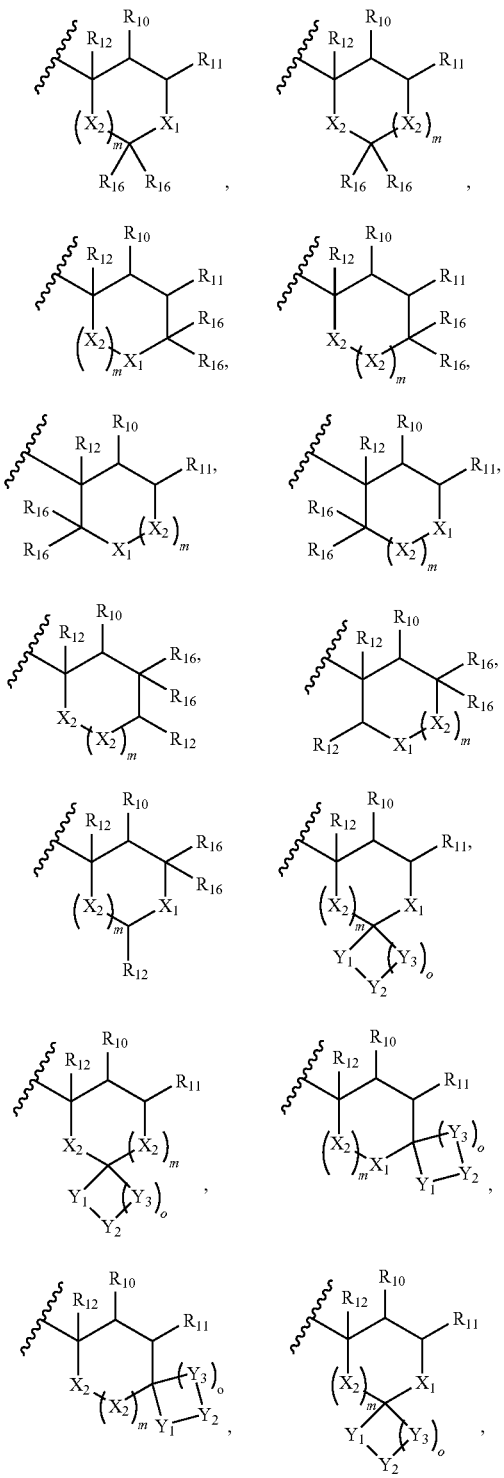

-continued

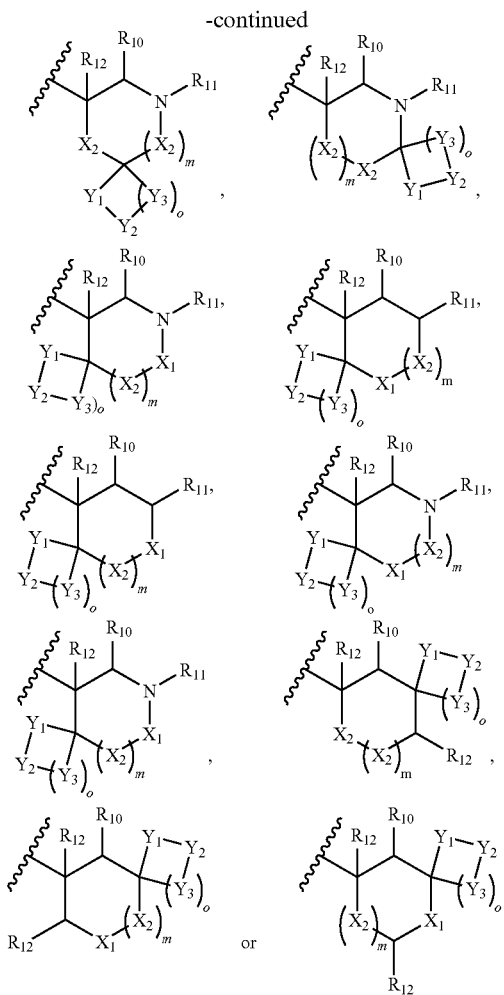

wherein $X^1$ is C(=O), O, S or $NR^{12}$;
each $X^2$, independently, is $CR^{12}R^{12}$;
each of $Y^1$, $Y^2$ and $Y^3$, independently, is $CR^{12}R^{12}$, O, S or $NR^{12}$;
m is 0, 1 or 2; and
o is 0, 1, 2, 3, 4 or 5;
provided that (a) no more than one of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benyl or phenyl;

$R^{10}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$ and optionally fused to a 4-7 membered third ring, the third ring formed of carbon atoms optionally including 1-3 heteroatoms selected from O, N, or S, and optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$; and $R^{15}$ is H, halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, the compounds of Formula III include each independent embodiment, as described herein for variables $R^1$, $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, B, W, V, $X^1$, $X^2$, $Y^1$, $Y^2$, $Y^3$, $Z^1$ and $Z^2$ for compounds of Formula I, independently, in conjunction with any of the above or below embodiments for compounds of Formula III.

In another embodiment, the invention provides each of the Examplary compounds, and stereoisomers, tautomers, solvates, pharmaceutically acceptable salts, derivatives or prodrugs thereof, and related intermediates, described herein.

Definitions

The following definitions should assist in understanding the invention described herein.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$-alkyl", when used either alone or within other terms such as "haloalkyl" and "alkylamino", embraces linear or branched radicals having α to β number of carbon atoms (such as $C_1$-$C_{10}$). One or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$alkoxyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 5-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include C$_3$-C$_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimetbylamino, N,N-diethylamino, and the like.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)$NH_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "haloalkylthio" embraces radicals containing a haloalkyl radical, of one to ten carbon atoms, attached to a divalent sulfur atom. An example of "haloalkylthio" is trifluoromethylthio.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the term "Formula II" includes any sub formulas and "Formula III" includes any sub formulas.

The term "pharmaceutically-acceptable" when used with reference to a compound of Formulas I-III is intended to refer to a form of the compound that is safe for administration. For example, a salt form, a solvate, a hydrate or derivative form of a compound of Formula I, II or of Formula III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuiric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-III. A "pharmaceutically-acceptable prodrug" as used herein, denotes a prodrug which is pharmaceutically acceptable. Pharmaceutically acceptable modifications to the compounds of Formula I-III are readily appreciated by those of ordinary skill in the art.

The compound(s) of Formulas I-III may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, II and III.

The compounds of Formulas I-III can be synthesized according to the procedures described in the following Schemes 1-5, wherein the substituents are as defined for Formulas I, II and III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
BOP—benzotriazol-1-yl-oxy hexafluorophosphate
$Cs_2CO_3$—cesium carbonate
$CHCl_3$—chloroform
$CH_2Cl_2$, DCM—dichloromethane, methylene chloride
CuI—copper iodide
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
$NaBH_4$—sodium borohydride
NaOH—sodium hydroxide
$Na_2SO_4$—sodium sulfate NH₄Cl—ammonium chloride
NH₄OH—ammonium hydroxide
P(t-bu)₃—tri(tert-butyl)phosphine
PBS—phospate buffered saline
Pd/C—palladium on carbon
Pd(PPh₃)₄—palladium(0)triphenylphosphine tetrakis
Pd(dppf)Cl₂—palladium(1,1-bisdiphenylphosphinoferrocene) II chloride
Pd(PhCN)₂Cl₂—palladium di-cyanophenyl dichloride
Pd(OAc)₂—palladium acetate
Pd₂(dba)₃—bis(dibenzylideneacetone)palladium
PyBop—benzotriazol-1-yl-oxy-tripyrrolidino-phosphonium hexafluorophosphate
RT, rt—room temperature
RBF, rbf—round bottom flask
TBTU—O-benzotriazol-1-yl-N,N,N',N'-tetramethyluronium tetrafluoroborate
TEA, Et₃N—triethylamine
TFA—trifluoroacetic acid
THF—tetrahydrofuran
UV—ultraviolet light

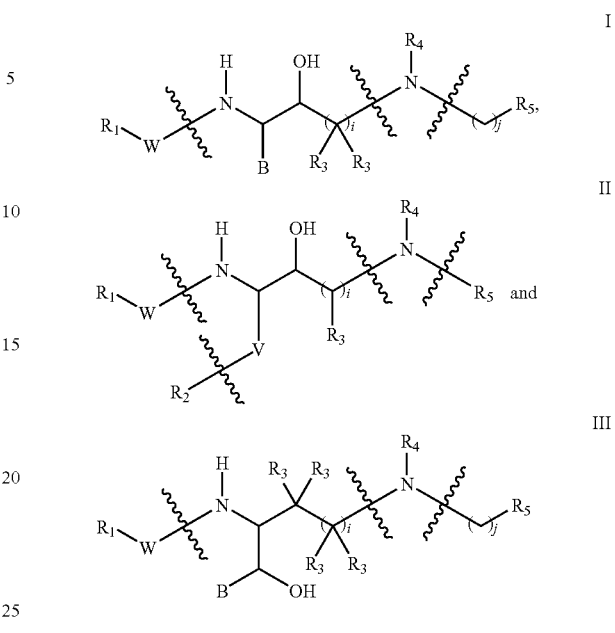

While the synthetic strategy for preparing the compounds of Formulas I, II and III may vary, as appreciated by persons skilled in the art, one strategy for devising a method of making compounds of these formulas is by retro-synthetic disconnection. For example, as shown in Formulas I-III above, each squiggly line represents a possible point of bond-construction, whose order is generally dependent upon the particular compound being synthesized. Such bond construction methods are generally described in synthetic Schemes 1-5 below.

Scheme 1

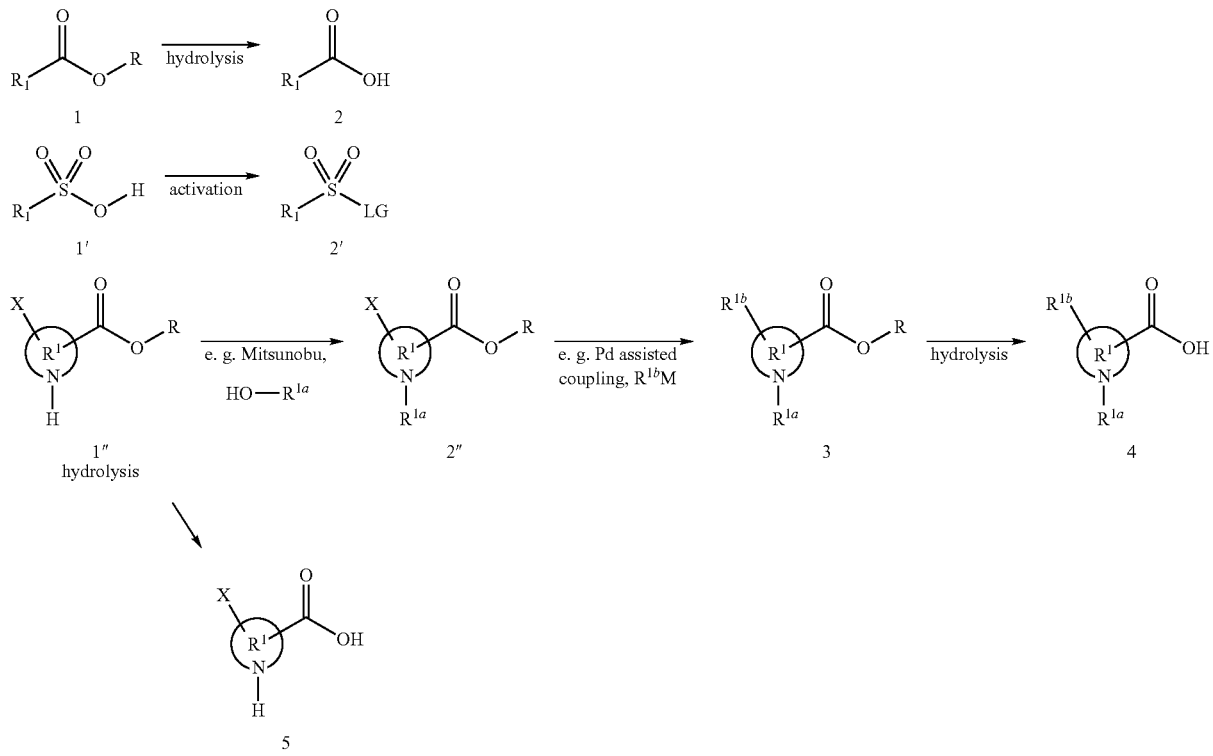

wherein, R is C1–C4 alkyl, e.g., $CH_3$, $C_2H_5$, etc. and e.g., X = Br, I, Cl, etc.; $R^{1b} = R^{1b}B(OH)_2$, $R^{1b}SnBu_3$, etc.

Scheme 1 describes a few methods for preparing $R^1$-W acids, useful for preparing compounds of Formulas I-III (see scheme 2) wherein W is —C(O)— or —S(O)$_2$— and $R^1$ is a fully unsaturated 5-8 membered monocyclic, 6-12 membered bicyclic, or 7-14 membered tricyclic ring system, said ring system formed of carbon atoms and optionally including one or more heteroatoms. Desired $R^1$-W groups may be commercially available and purchased, or may be made by known, conventional methods. As shown, esters 1 can be hydrolyzed to their corresponding acids 2 using known bases, such as NaOH or LiOH. Acids 2 can then be coupled to an amine (not shown) to prepare compounds of Formula I-III. Similarly, sulfonic acids 1' can be converted to an activated sulfonate 2' by reaction with oxalyl chloride, for example, to prepare the corresponding sulfonyl chloride 2'. The sulfonyl chloride 2' can be reacted with an amine to prepare compounds of Formula I-III.

In a similar manner, a desired ring $R^1$ of compounds 1'' may first be functionalized prior to coupling to the amino-backbone, as shown in scheme 2. An ester-halo (X=halogen such as Br or I) substituted $R^1$ ring acid 4 or 5, both of which include a substitutable nitrogen in the ring, and which are generally referred to herein as the left-hand portion of the compounds of Formulas I, II and III, can be prepared according to the method generally described in the second half of Scheme 1. As shown, a methyl ester-halo substituted compound 1'' can be reacted in a Mitsunobu-type reaction with a desired hydroxyl-substituted $R^{1a}$ compound under suitable conditions, such as in the presence of tri-phenyl phosphine and diethylazodicarboxylate (commonly referred to as DEAD) for a suitable time period to form the ring N—$R^{1a}$ substituted adduct 2''. Intermediate 2'' may also be formed using a suitable reductive amination method as well utilizing an aldehyde, for example (not shown in scheme 1). Compound 2'' can be reacted in a palladium-catalyzed coupling reaction, such as a suzuki-type reaction, in the presence of suitable solvents and accompanying reagents, such as a base, to form the $R^1$-$R^{1b}$ substituted compound 3. Formation of compound 3 may require heat, up to and including reflux temperatures depending on the particular substrate, solvent and reagent(s) concentration, as appreciated by those skilled in the art. Compound 3 can then be hydrolyzed in the presence of a suitable base and solvent to form the corresponding acid-adduct 4. Acid 4 is then utilized as an intermediate to couple, as described in scheme 2 below, with desired intermediates or other building blocks to make compounds of Formulas I-III.

Alternatively, compound 1'' can be hydrolyzed directly to the corresponding acid 5. Ester-Halo-substituted compound 5 is a useful intermediate for coupling the backbone core compounds with desired B, $R^3$ and $R^4$ substitutions already in place. Compound 5 can then be modified to include desirable $R^1$ substitutions, including $R^{1a}$, $R^7$, $R^8$ and $R^9$ groups. In this fashion, analogs of a variety of desired left-hand pieces of compounds of Formulas I-III may be readily synthesized (see scheme 3).

By known methods, the acids 1', 2, 4 and 5, may be converted to the corresponding isocycanates and then reacted with an amine (not shown) to make an $R^1$-urea linked group (where W=—NHC(O)—).

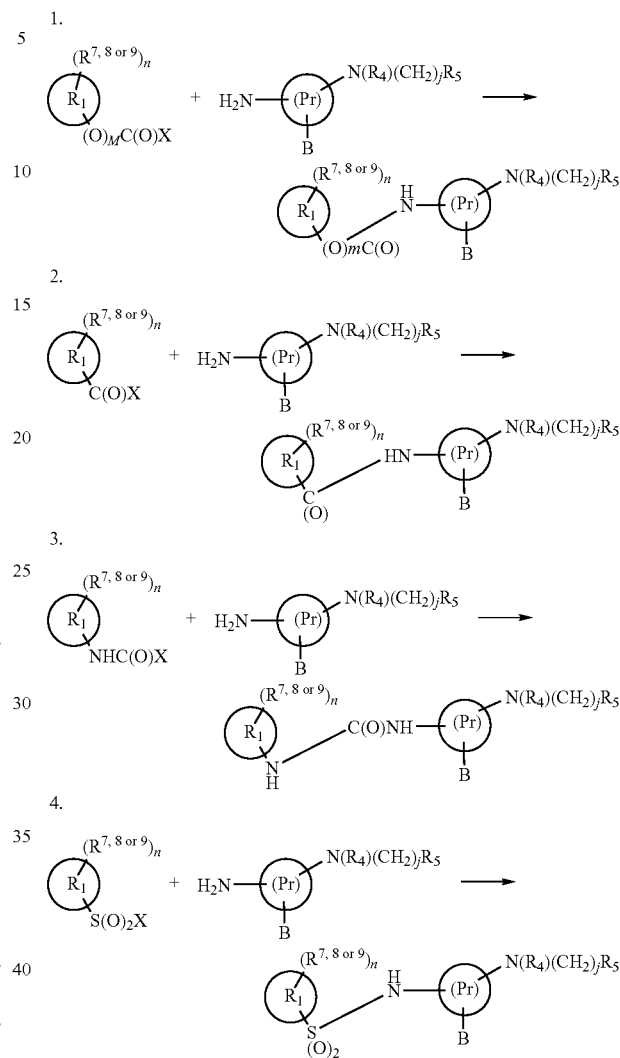

Scheme 2

Desired $R^1$-W groups, which may be substituted with various substitutions including one or more $R^7$, $R^8$ or $R^9$ groups, can be coupled to the core hydroxyl-propyl, hydroxyl-butyl or hydroxyl-pentyl backbone structure, generally designated in Scheme 2 as "Pr" group, by various coupling methods as described in Scheme 2. In each of the 4 sub-schemes, X refers generally to a "LG" or a "leaving group" such as a halide (bromine, chlorine, iodine or fluorine), alkylsulfonate and other known groups (also see definitions herein) which generally forms an electrophilic species (E$^+$) and m is an integer from 0-1. The NH$_2$ group (primary amine) is a nucleophilic species (Nu$^-$), as is secondary amines, hydroxides, alkoxides, an anionic carbon species and the like, which should be sufficiently strong to the attack the E$^+$ species and displace the leaving group X thereby effecting a coupling of $R^1$-W to the Pr backbone. Examples of suitable electrophilic carbonyl species include, without limitation, acid halides, mixed anhydrides, aldehydes, carbamoyl-chlorides, sulfonyl chlorides, acids activated by coupling with activating reagents such as TBTU, HBTU, HATU, HOBT, BOP, PyBOP and carbodiimides (DCC, EDC and the like), and other electrophilic species including halides, isocyanates, daizonium ions and the like.

The coupled adduct of $R^1$-W and Pr, shown as products in sub-schemes 1-4, can be brought about using various conventional methods. For example, an amide or a sulfonamide linkage, as shown in sub-schemes 2 and 4, can be made utilizing an amine on the Pr intermediate and an activated electrophilic species, on the $R^1$-W group such as the acid chloride or sulfonyl chloride as shown. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art.

Similarly, carbamates as illustrated in sub-scheme 1 and ureas as illustrated in sub-scheme 3 may be made as shown, wherein X has the same definition as above, using the same coupling methods described above for sub-schemes 2 and 4. While the above methods are so described, they are not exhaustive, and other methods for linking $R^1$-W groups and desired Pr groups together may be utilized as appreciated by those skilled in the art.

The coupling methods described in sub-schemes 1-4 of scheme 2 are also applicable for coupling desired $R^1$-W intermediates to desired Pr intermediates not containing desired $R^5$ groups, although sub-schemes 1-4 as illustrated do contain $R^5$ groups.

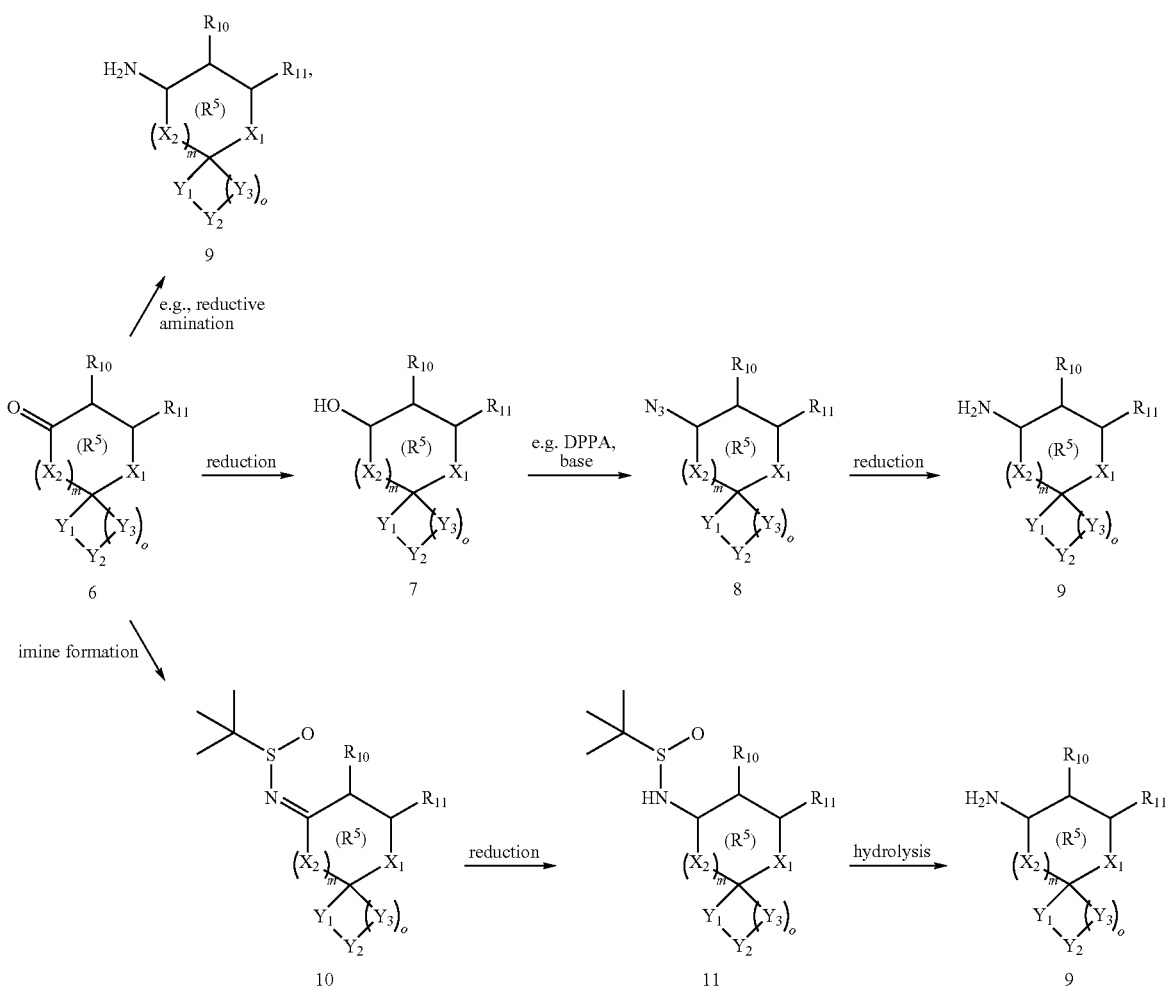

Scheme 3

Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Amine intermediate 9 (j=0) can be prepared according to the method generally described in Scheme 3. As shown, spiro-substituted- or gem-dialky-substituted (not shown) oxo-$R^5$ ring intermediates 6 can be converted directly to the amino-intermediate 9 using known reductive amination methods, such as in the presence of sodium cyanoborohydride and ammonium acetate. Alternatively, the carbonyl of $R^5$ may be reduced to the corresponding alcohol using conventional reducing reagents, and then displaced to form the corresponding azido-intermediate 8 using known reagents, such as DPPA, in the presence of a suitable base as shown. Intermediate 8 may be reduced with a suitable reducing agent or by known methods, including triphenylphosphene, trimethylphosphene or lithium aluminum hydride (LAH), to produce the desired amino adduct 9.

Yet another method of forming the amine adduct 9, can be via an imine formation to form compound 10. The imine double bond of compound 10 may then be successively reduced and hydrolyzed to yield the primary amine product 9. Such steps may be conducted using known, convention methods, as appreciated by those skilled in the art.

Scheme 4

1.

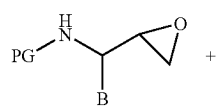

PG = protecting group
12'

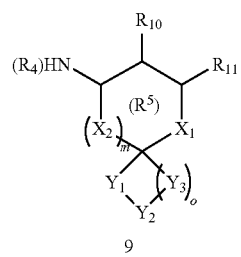

9

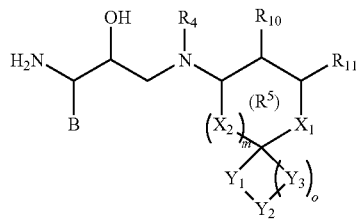

14'

2.

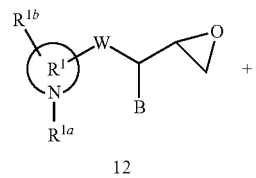

12

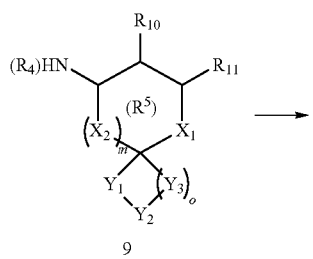

9

-continued

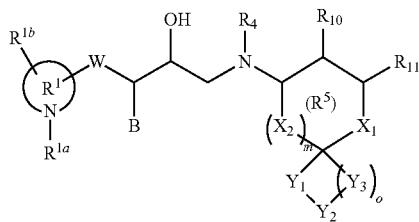

14

3.

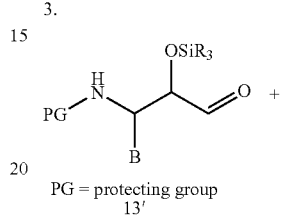

PG = protecting group
13'

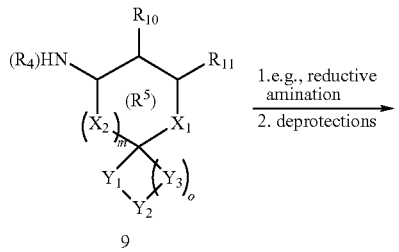

9

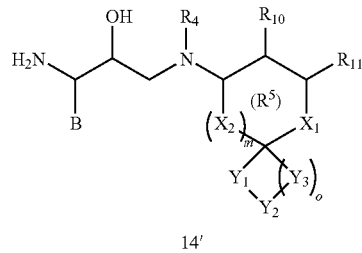

14'

4.

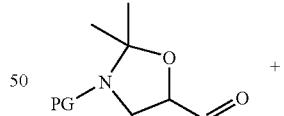

PG = protecting group
13

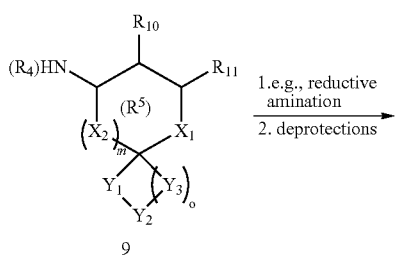

9

-continued

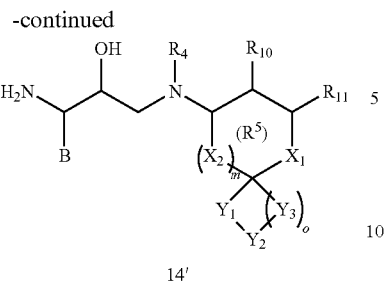

14'

Scheme 4 describes, generally, multiple different methods for constructing the bond between the Pr starting material or intermediate 12' (sub-scheme 1) or 12 (sub-scheme 2) and an R⁵ ring intermediate 9, thereby synthesizing a desired intermediate 14' or a final compound 14 of Formulas I-III. One method to make this bond is to react an epoxide intermediate 12 or 12' (Note: the epoxide 12 or 12' may be purchased commercially or made via known, published methods such as from the olefin precursor), with an amino-R⁵ intermediate 9, as shown. The reaction may proceed in the presence of a polar solvent, such as an alcohol or dioxanes, and may require additional reagents, as appreciated by those skilled in the art. Additionally, the reaction may require heat for a period of time. Note that while the scheme described the addition o heat, this is by way of example, and not every reaction would require heat as appreciated by those of ordinary skill in the art. The protecting group may be removed using an acid, such as HCl, such that the bonded adduct 14' is recovered as an HCl salt.

Alternatively, desired intermediates 14' may be synthesized starting with an amine-protected aldehyde intermediate 13' (sub-scheme 3) or 13 (sub-scheme 4) and condensing the aldehyde with a primary or secondary amine 9 to form an imine (not shown, generally formed in-situ and not isolated). The imine can then be reduced using a known reducing agent, such as a hydride or borohydride, the reduced intermediate may be deprotected to provide an intermediate 14' having an amine useful to prepare compounds 14 of Formulas I-III.

Scheme 5

Method A:

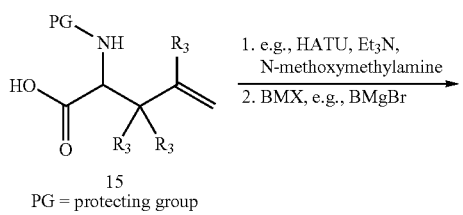

15
PG = protecting group

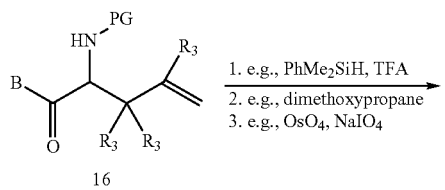

16

-continued

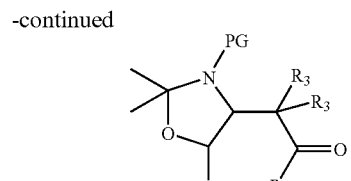

17

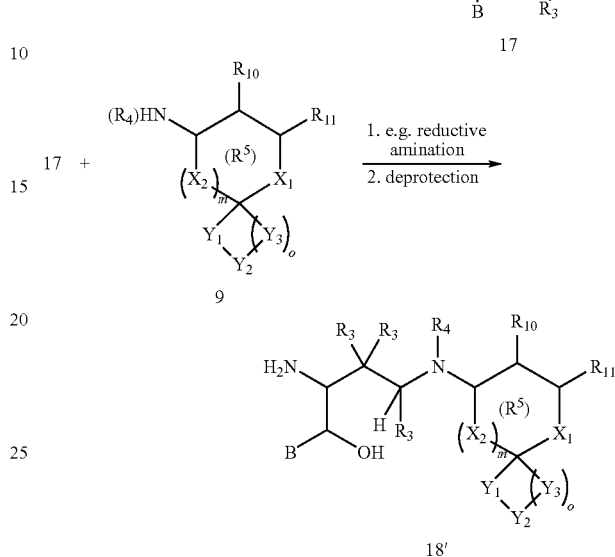

Method B:

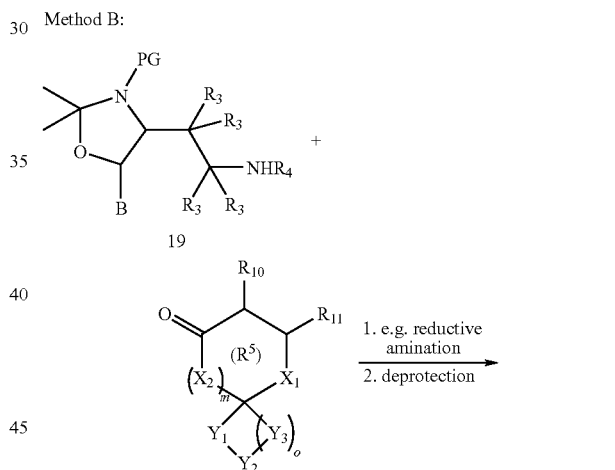

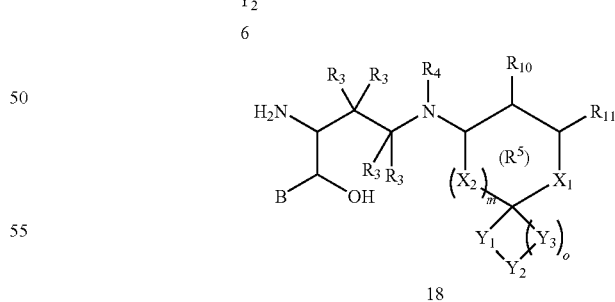

Scheme 5 describes, generally, two different methods (Methods A and B) for constructing intermediates 18' (Method A) or 18 (Method B) which are useful for making compounds of Formula III. As shown in Method A, the acid group of an olefinic amino-acid compound 15 may be modified with a desired B group to form a compound 16, by first activating the acid of 15 with a known activating agent, such as HATU in the presence of a suitable base, and treating activated 15 with a B-substituted grignard reagent or B-ligand metal reagent, which delivers the desired B group to displace the carbonyl activating group and form compound 16. Compound 16 may be oxidized to the corresponding ketone 17 by known methods, such as with sodium periodiate and osmium tetroxide. Ketone 17 may then be reacted with amine 9, via a reductive amination step, to form an amino protected intermediate, which can be deprotected to yield intermediate 18', as shown.

Alternatively, intermediate 18 may be made using a reductive amination step with an amine-protected diamine compound 19 and a ketone 6. Such reductive amination step may be employed with conventional conditions using known reducing reagents in suitable solvents, at suitable temperatures, as appreciated by one of ordinary skill in the art.

Amine compounds 18 and 18' can then be coupled to acids and sulfonic acid compounds 2, 2', 4 and 5, described in scheme 1, to make amides and sulfonamide compounds ("W" groups) of Formulas I-III by methods described in scheme 2.

To enhance the understanding and appreciation of the present invention, the following specific examples (starting reagents, intermediates and compounds of Formulas I-III) are set forth. The following analytical methods were used to purify and/or characterize the compounds, and intermediates, described in the examples below.

Analytical HPLC and LC-MS Methods:

Unless otherwise indicated, all analytical HPLC analyses were run on an Agilent Model 1100 series system LC/MSD SL using one of the two following Columns: (a) Phenomenex Semegi (4 micron, C18, 50×2 mm) or (b) a Gemini column (5 micron, C18, 100×2 mm). A typical run through the instrument included: eluting at 1 ml/min with an linear gradient of 10% (v/v) to 100% MeCN (0.1% v/v TFA) in water (0.1% TFA) over 10 minutes; conditions may be varied to achieve optimal separation.

Preparative BPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument.

Compounds having an isotopic atom, such as bromine and the like, are generally reported according to the detected isotopic pattern, as appreciated by those skilled in the art.

Naming Convention

The compounds disclosed and described herein have been named using the naming convention provided with Chem-Draw Ultra 8.0 software, available in Chem Office. In some instances, compounds were named with the term "spirocarbocycle" inserted where appropriate. For example, where the chroman is substituted with 2,2-spirocyclobutyl, "2,2-spirocyclobutyl" is added to the Chem-Draw nomenclature in the appropriate place. Chem-Draw utilizes the ISIS Draw software compound naming convention, as appreciated by those skilled in the art.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I, II and III. It should be appreciated that the general methods above and specific examples below are illustrative only, for purpose of assistance, and should not be construed as limiting the scope of the present invention in any manner.

Example 1

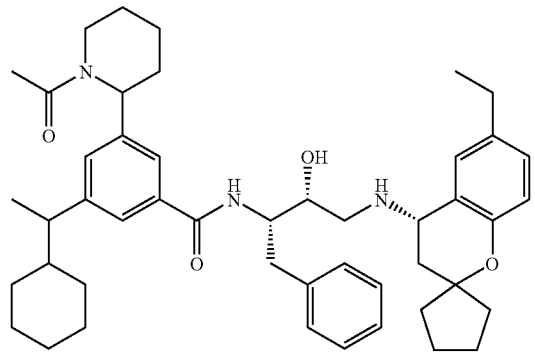

3-(1-acetylpiperidin-2-yl)-5-(1-cyclohexylethyl)-N-((2S,3R)-4-((S)-6-ethyl-2,2-spirocyclopentylchroman-4-ylamino)-3-hydroxy-1-phenylbutan-2-yl)benzamide Step 1: Methyl 3-bromo-5-(pyridin-2-yl)benzoate To an argon purged solution of methyl 3-bromo-5-iodobenzoate (834 mg, 2.45 mmol) and Pd(PPh$_3$)$_4$ (142 mg, 0.12 mmol) in THF (20 mL) was added 2-pyridylzinc chloride (0.5 M, 7.4 mL, 3.7 mmol). The mixture was stirred overnight and then poured into a large volume of water (100 mL). The resulting solution was extracted with EtOAc (3×20 mL) and the combined organics were successively washed with water (1×20 mL), brine (1×20 mL), dried over sodium sulfate, filtered and concentrated under reduced pressure. The crude residue was purified via automated flash chromatography (silica gel; 0 to 25% EtOAc in hexanes) to afford methyl 3-bromo-5-(pyridin-2-yl)benzoate. MS m/z=292, 294 [M+1]$^+$; Calc'd for C$_{13}$H$_{10}$BrNO$_2$: 292.

Step 2: Methyl 3-(1-12henylvinyl)-5-(pyridin-2-yl)benzoate

Methyl 3-bromo-5-(pyridin-2-yl)benzoate (137 mg, 0.47 mmol), 4,4,5,5-tetramethyl-2-(1-phenylvinyl)-1,3,2-dioxaborolane (162 mg, 0.70 mmol), Pd(PPh$_3$)$_4$ (19 mg, 0.023 mmol) and K$_2$CO$_3$ (195 mg, 1.41 mmol) were taken up in DME (5 mL) and water (1 mL) and heated to about 80° C. overnight. The reaction mixture was combined with water and the product was extracted into EtOAc (3×10 mL). The combined organic extracts were washed with water (1×10 mL), brine (1×10 mL), dried over sodium sulfate, filtered and concentrated under reduced pressure. The crude residue was purified via automated flash chromatography (silica gel; 0 to 25% EtOAc in hexanes) to afford methyl 3-(1-phenylvinyl)-5-(pyridin-2-yl)benzoate. MS m/z=316 [M+1]⁺. Calc'd for $C_{21}H_{17}NO_2$: 315.

Step 3: Methyl 3-(1-acetylpiperidin-2-yl)-5-(1-cyclohexylethyl)benzoate

To an argon purged solution of methyl 3-(1-phenylvinyl)-5-(pyridin-2-yl)benzoate (73 mg, 0.23 mmol) in ethanol (5 mL) and HCl (conc. 1 mL) was added PtO₂ (7 mg, 0.023 mmol). The mixture was hydrogenated under a hydrogen atmosphere (35 psi) for 6 h. The reaction mixture was purged with argon, filtered through a 0.2 μm filter, and concentrated. The resulting crude material was taken up with CH₂Cl₂ (5 mL) after which $^i$Pr₂NEt (0.1 mL, 0.58 mmol) and acetyl chloride (18 μL, 0.25 mmol) were successively added. The mixture was stirred for 30 min, then diluted with CH₂Cl₂ (30 mL) and washed successively with 0.5 M HCl (1×10 mL), 9% sodium carbonate (1×10 mL), brine, dried over sodium sulfate, filtered and concentrated under reduced pressure. The crude residue containing the title compound was used without further purification. MS m/z=372 [M+1]⁺; Calc'd for $C_{23}H_{33}NO_3$: 371.

Step 4: 3-(1-acetylpiperidin-2-yl)-5-(1-cyclohexylethyl)benzoic acid

To a solution of 3-(1-acetylpiperidin-2-yl)-5-(1-cyclohexylethyl)benzoate (80 mg, 0.22 mmol) in THF:MeOH:water (1:1:1, 6 mL) was added NaOH (6 N, 10 drops) and the mixture was stirred for 3 h. The volatiles were removed in vacuo and the mixture was acidified with aqueous HCl (6 N) to a pH of about 2. The mixture was extracted with EtOAc (3×10 mL). The combined organics were washed with water (1×10 mL), brine (1×10 mL), dried over sodium sulfate, filtered and concentrated. The title compound was used without further purification.

Step 5: 3-(1-acetylpiperidin-2-yl)-5-(1-cyclohexylethyl)-N-((2S,3R)-4-((S)-6-ethyl-2,2-spirocyclopentylchroman-4-ylamino)-3-hydroxy-1-phenylbutan-2-yl)benzamide The benzoic acid from step 4 (20 mg) was dissolved in DMF (0.5 mL), and DIPEA (0.1 mL) and HATU (42 mg, 0.11 mmol) were added to the reaction. In a separate flask was mixed (2R,3S)-3-amino-1-((S)-6-ethyl-2,2-spirocyclopentyl-chroman-4-ylamino)-4-phenylbutan-2-ol, bis HCl salt (40 mg, 0.085 mmol), DIPEA (0.1 mL) and DMF (0.5 mL) and the mixture was stirred for 10 min and then added to the benzoic acid/HATU mixture. The combined mixture was stirred for 1 h and the title compound was purified by reverse phase HPLC by directly loading the reaction mixture onto a reverse phase HPLC column. The pure fractions were concentrated to provide the title compound. MS m/z=734(M+1).

Example 2

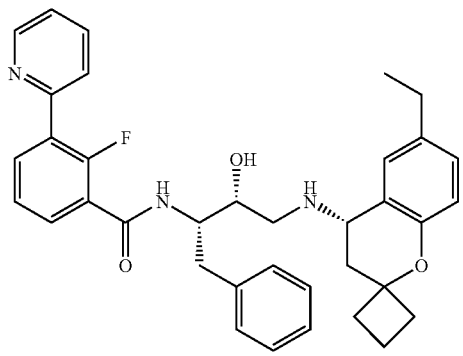

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-fluoro-3-(2-pyridinyl)benzamide Step 1: Methyl 3-bromo-2-fluorobenzoate To a 100 mL round bottom flask was added 3-bromo-2-fluorobenzoic acid (5.00 g, 22.8 mmol, Oakwood), potassium carbonate (3.17 g, 22.9 mmol), and DMF (30 mL). Iodomethane, 2 M in MTBE (11.6 ml, 23.2 mmol) was added and the reaction mixture was stirred at RT for 16 hours. The reaction was filtered and the filtrate concentrated was in vacuo. The resulting brown crude residue was taken up with EtOAc and again filtered and concentrated to give methyl 3-bromo-2-fluorobenzoate (4.76 g, 20.4 mmol, 89.5% yield), as a brown syrup that was used in the Step 2 without further purification.

Step 2: 2-Fluro-3-(pyridine-2-yl)benzoic acid

In a 150 mL round bottom flask was combined methyl 3-bromo-2-fluorobenzoate (1.47 g, 6.3 mmol), DMF (10 mL), silver oxide (0.79 g, 6.4 mmol), 2-(tributylstannyl)pyridine (2.40 ml, 7.2 mmol), and dichlorobis(triphenylphosphine)-palladium (II) (0.23 g, 0.33 mmol) and the mixture was stirred at 100° C. to about 72 h. Monitoring the reaction by LC-MS revealed two products, the ester and the hydrolyzed product. The reaction was cooled, filtered through a pad of celite and the celite was washed with EtOAc. The filtrate was concentrated in vacuo and taken up in a small amount of DMF. The solution was purified by reverse-phase preparative HPLC on a Phenomenex Luna column (10 micron, C18, 100 Å, 150×50 mm) eluting at 45 ml/min with an linear gradient of 10% (v/v) to 100% MeCN (0.1% v/v TFA) in water (0.1% TFA) over 10 minutes to give 2-fluoro-3-(pyridine-2-yl)benzoic acid (0.24 g, 0.72 mmol, 23% yield) as a light red-colored TFA salt and methyl 2-fluoro-3-(pyridine-2-yl)benzoate (0.19 g, 0.55 mmol, 17% yield) as a golden syrup-colored TFA salt.

Step 3: N-((1S,2R)-3-(((4S)-6-ethyl-3,4-dihydrospiro[chromene-2,1'-cyclobutan]-4-yl)amino)-2-hydroxy-1-(phenylmethyl)propyl)-2-fluoro-3-(2-pyridinyl)benzamide The benzoic acid from Step 2 was dissolved in DMF, and DIPEA and HATU were added to the reaction. In a separate flask was mixed (2R,3S)-3-amino-1-((S)-6-ethyl-2,2-spirocyclobutyl-chroman-4-ylamino)-4-phenylbutan-2-ol, DIPEA and DMF and the mixture was stirred for 10 min and then added to the benzoic acid/HATU mixture. The combined mixture was stirred for 1 h and the title compound was purified by reverse phase HPLC by directly loading the reaction mixture onto a reverse phase HPLC column. The pure fractions were concentrated to provide the title compound. MS m/z=580 (M+1).

Example 3

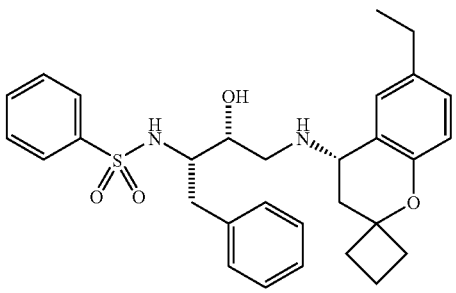

N-((2S,3R)4-((S)-6ethyl-2,2-spirocyclobutyl-chroman-4ylamino)-3-hydroxy-1-phenylbutan-2-yl)benzenesulfonamide To a solution of (2R,3S)-3-amino-1-((S)-6-ethyl-2,2-spirocyclobutyl-chroman-4-ylamino)-4-phenylbutan-2-ol (see application Ser. Nos. 60/738,765 and 60/738,766 assigned to same applicant for details of synthesis) (50.0 mg, 0.111 mmol) and pyridine (0.500 mL) in 1.11 mL of DCM was added benzenesulfonyl chloride (14.1 µL, 0.111 mmol) at RT. After stirring overnight, the crude reaction mixture was concentrated to yield an oil, which was dissolved in about 1 ml of ACN and purified by HPLC on a Gilson HPLC column. The title compound was obtained. MS m/z=521 (M+1).

Example 4

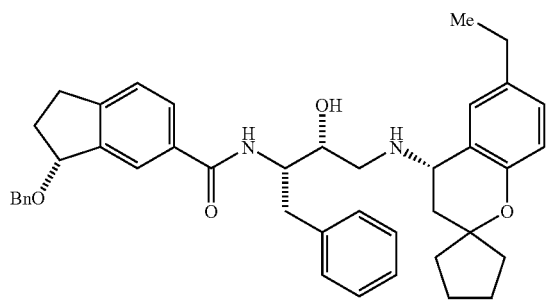

(R)-3-(benzyloxy)-N-((2S,3R)-4-((S)-6-ethyl-2,2-spirocyclopentyl-chroman-4-ylamino)-3-hydroxy-1-phenylbutan-2-yl)-2,3-dihydro-1H-indene-5carboxamide step 1: 2-(Trimethylsilyl)ethyl 3-oxo-2,3-dihydro-1H-indene-5-carboxylate To a solution of acid (570 mg, 3.24 mmol), TMS ethanol (1.86 mL, 12.9 mmol), DMAP (198 mg, 1.62 mmol) in 16.2 mL of DMF was added DIC (0.602 mL, 3.89 mmol). The resulting solution was stirred overnight. The crude reaction mixture was then transferred to a seperatory funnel containing EtOAc, and water. The water layer was washed 3× with EtOAc, the organic layers were combined, dried with MgSO4, filtered and concentrated to yield an oil. The crude oil residue was purified with the Biotage MPLC (grad: 100% Hex to 80/20 Hex/EtOAc) to afford the title compound (718 mg; 80% yield).

step 2: (S)-2-(Trimethylsilyl)ethyl 3-hydroxy-2,3-dihydro-1H-indene-5-carboxylate To a solution of R-CBS reagent (90 µL, 1M sol.) and BH$_3$DMS (220 µL, 2.34 mmol) in 3.6 ml of toluene at −10° C. was dropwise added over about 2 h, a solution of the product from Step 1 (500 mg, 1.8 mmol) in 1.8 mL of THF. After addition was complete, the reaction mixture was quenched with 0.5 N HCl. The resulting mixture was transferred to a seperatory funnel and the aqueous layer was washed 3× with EtOAc. The organic layers were combined, dried over MgSO4, filtered and concentrated to yield an oil, which was was purified by chiral HPLC (77% ee prior to chiral separation) to afford the title compound.

step 3: (S)-Benzyl 3-(benzyloxy)-2,3-dihydro-1H-indene-5-carboxylate

To a solution of the alcohol from Step 2 (140 mg, 0.503 mmol) was added NaH (28.2 mg, 1.18 mmol) in one portion at RT. After stirring for 30 min, BnCl (116 µL, 1.01 mmol) was added dropwise and the resulting mixture was stirred overnight. The excess NaH was quenched with water and the mixture was transferred to a seperatory funnel where the aqueous layer was washed 3× with DCM. The organic layers were combined, dried with MgSO$_4$, filtered and concentrated to yield an oil. The title compound was purified on a Biotage MPLC (grad: 100% Hex to 60% EtOAc in Hex).

step 4: (S)-3-(Benzyloxy)-2,3-dihydro-1H-indene-5-carboxylic acid

To a solution of the title compound of Step 3 (62.7 mg, 0.175) in 1.00 ml of THF was added 1.00 ml of 6 N NaOH and 1.00 ml MeOH. The resulting mixture was stirred overnight. The mixture was acidified to neutral pH, concentrated and the title compound was purified on a Biotage MPLC.

step 5: (R)-3-(benzyloxy)-N-((2S,3R)-4-((S)-6-ethyl-2,2-spirocyclopentyl-chroman-4-ylamino)-3-hydroxy-1-phenylbutan-2-yl)-2,3-dihydro-1H-indene-5-carboxamide The title compound was obtained using (2R,3S)-3-amino-1-((S)-6-ethyl-2,2-spiorcyclopentyl-chroman-4-ylamino)-4-phenylbutan-2-ol in a method analogous to step 5 of Example 3 above. MS m/z=645(M+1).

The following examples were prepared by a method analogous to those described in Examples 1-4 above.

| Ex. No. | Name | MW | Mass Found |
|---|---|---|---|
| 5 | 3-cyclopentyl-N-((2S,3R)-4-((S)-6-ethy-2,2-spirocyclopentylchroman-4-ylamino)-3-hydroxy-1-phenylbutan-2-yl)-5-(1-(methylsulfonyl)piperidin-2-yl)benzamide | 1456.01 | 728 |
| 6 | 3-(1-acetylpiperidin-2-yl)-5-cyclopentyl-N-((2S,3R)-4-((S)-6-ethyl-2,2-spirocyclopentylchroman-4-ylamino)-3-hydroxy-1-phenylbutan-2-yl)benzamide | 1383.9 | 692 |
| 7 | 3-cyclopentyl-N-((2S,3R)-4-((S)-6-ethyl-2,2-spirocyclopentylchroman-4-ylamino)-3-hydroxy-1-phenylbutan-2-yl)-5-(2-fluorophenyl)benzamide | 660.869 | 661 |
| 8 | 3-cyclopentyl-N-((2S,3R)-4-((S)-6-ethyl-2,2-spirocyclopentylchroman-4-ylamino)-3-hydroxy-1-phenylbutan-2-yl)-5-(phenyl)benzamide | 642.879 | 643 |
| 9 | 3-cyclopentyl-N-((2S,3R)-4-((S)-6-ethyl-2,2-spirocyclopentylchroman-4-ylamino)-3-hydroxy-1-phenylbutan-2-yl)-5-(thiophen-2-yl) benzamide | 648.907 | 649 |
| 10 | 3-(1-acetylpyrrolidin-2-yl)-5-cyclopentyl-N-((2S,3R)-4-((S)-6-ethyl-2,2-spirocyclopentylchroman-4-ylamino)-3-hydroxy-1-phenylbutan-2-yl)benzamide | 1355.85 | 678 |
| 11 | 3-(1-acetylpiperidin-2-yl)-5-cyclohexyl-N-((2S,3R)-4-((S)-6-ethyl-2,2-spirocyclopentylchroman-4-ylamino)-3-hydroxy-1-phenylbutan-2-yl)benzamide | 1411.96 | 706 |
| 12 | 3-((2S)-1-acetyl-2-pyrrolidinyl)-5-cyclopentyl-N-((1S,2R)-2-hydroxy-1-(phenylmethyl)-3-(((3-(trifluoromethyl)phenyl)methyl)amino)propyl)benzamide 3-((2R)-1-acetyl-2-pyrrolidinyl)-5-cyclopentyl-N-((1S,2R)-2-hydroxy-1-(phenylmethyl)-3-(((3-(trifluoromethyl)phenyl)methyl)amino)propyl)benzamide | 1243.48 | 622 |
| 13 | 3-((2R)-1-acetyl-2-piperidinyl)-N-((1S,2R)-3-(((4S)-6-ethyl-3,4-dihydrospiro[chromene-2,1'-cyclopentan]-4-yl)amino)-2-hydroxy-1-(phenylmethyl)propyl)-5-(1-pyrrolidinyl) benzamide | 1385.88 | 693 |
| 14 | 3-(1-acetyl-2-piperidinyl)-5-((3S)-1-acetyl-3-pyrrolidinyl)-N-((1S,2R)-3-(((4S)-6-ethyl-3,4-dihydrospiro[chromene-2,1'-cyclopentan]-4-yl)amino)-2-hydroxy-1-(phenylmethyl)propyl)benzamide | 2939.9 | 735 |

-continued

| Ex. No. | Name | MW | Mass Found |
|---|---|---|---|
| 15 | 3-((2S)-1-acetyl-2-piperidinyl)-N-((1S,2R)-3-(((4S)-6-ethyl-3,4-dihydrospiro[chromene-2,1'-cyclopentan]-4-yl)amino)-2-hydroxy-1-(phenylmethyl)propyl)-5-((3S)-1-ethyl-3-pyrrolidinyl)benzamide | 2883.97 | 721 |
| 16 | 3-cyclopentyl-N-((2S,3R)-4-((S)-6-ethyl-2,2-spirocyclopentylchroman-4-ylamino)-3-hydroxy-1-phenylbutan-2-yl)-5-(thiazol-2-yl)benzamide | 649.895 | 650 |
| 17 | 3-(1-acetylpiperidin-3-yl)-5-cyclopentyl-N-((2S,3R)-4-((S)-6-ethyl-2,2-spirocyclopentylchroman-4-ylamino)-3-hydroxy-1-phenylbutan-2-yl)benzamide | 1383.9 | 692 |
| 18 | N-((2S,3R)-4-((S)-6-ethyl-2,2-spirocyclobutylchroman-4-ylamino)-3-hydroxy-1-phenylbutan-2-yl)-4-methylbenzamide | 498.663 | 499 |
| 19 | N-((2S,3R)-4-((S)-6-ethyl-2,2-spirocyclobutylchroman-4-ylamino)-3-hydroxy-1-phenylbutan-2-yl)pyrimidine-5-carboxamide | 486.613 | 487 |
| 20 | 5-bromo-N-((2S,3R)-4-((S)-6-ethyl-2,2-spirocyclobutylchroman-4-ylamino)-3-hydroxy-1-phenylbutan-2-yl)thiophene-3-carboxamide | 569.561 | 569.571 |
| 21 | 3-cyclopentyl-N-((2S,3R)-4-((S)-6-ethyl-2,2-spirocyclopentylchroman-4-ylamino)-3-hydroxy-1-phenylbutan-2-yl)-5-(1H-pyrrol-1-yl)benzamide | 631.856 | 632 |
| 22 | 3-(2-cyano-1H-pyrrol-1-yl)-5-cyclopentyl-N-((2S,3R)-4-((S)-6-ethyl-2,2-cyclopentyl-chroman-4-ylamino)-3-hydroxy-1-phenylbutan-2-yl)benzamide | 656.866 | 657 |
| 23 | 3-cyclopentyl-N-((2S,3R)-4-((S)-6-ethyl-2,2-cyclopentylchroman-4-ylamino)-3-hydroxy-1-phenylbutan-2-yl)-5-(2-oxopyrrolidin-1-yl)benzamide | 649.871 | 650 |
| 24 | 3-(3-cyano-1H-indol-1-yl)-5-cyclopentyl-N-((2S,3R)-4-((S)-6-ethyl-2,2-cyclopentyl-chroman-4-ylamino)-3-hydroxy-1-phenylbutan-2-yl)benzamide | 706.926 | 707 |
| 25 | 3-cyclopentyl-N-((1S,2R)-3-(((4S)-6-ethyl-2,2-dimethyl-3,4-dihydro-2H-chromen-4-yl)amino)-2-hydroxy-1-(phenylmethyl)propyl)-5-(2-oxo-1-pyrrolidinyl)benzamide | 623.833 | 624 |
| 26 | 3-(2-cyano-1H-pyrrol-1-yl)-5-cyclopentyl-N-((1S,2R)-3-(((4S)-6-ethyl-2,2-dimethyl-3,4-dihydro-2H-chromen-4-yl)amino)-2-hydroxy-1-(phenylmethyl)propyl)benzamide | 630.828 | 631 |
| 27 | N-((1S,2R)-1-((3-cyanophenyl)methyl)-3-(((4S)-6-ethyl-3,4-dihydrospiro[chromene-2,1'-cyclobutan]-4-yl)amino)-2-hydroxypropyl)-5-isoxazolecarboxamide | 500.596 | 501 |
| 28 | N-((2S,3R)-4-((S)-6-ethyl-2,2-spirocyclopentylchroman-4-ylamino)-3-hydroxy-1-phenylbutan-2-yl)benzamide | 498.663 | 499.3 |
| 29 | N-((2S,3R)-4-((S)-6-ethyl-2,2-spirocyclopentylchroman-4-ylamino)-3-hydroxy-1-phenylbutan-2-yl)-2-fluorobenzamide | 516.653 | 517.1 |
| 30 | N-((2S,3R)-4-((S)-6-ethyl-2,2-spirocyclopentylchroman-4-ylamino)-3-hydroxy-1-phenylbutan-2-yl)-2-methoxy-5-(2-oxopyrrolidin-1-yl)benzamide | 611.779 | 612.3 |
| 31 | 2-amino-N-((2S,3R)-4-((S)-6-ethyl-2,2-spirocyclopentylchroman-4-ylamino)-3-hydroxy-1-phenylbutan-2-yl)benzamide | 513.678 | 514.2 |
| 32 | N-((2S,3R)-4-((S)-6-ethyl-2,2-spirocyclopentylchroman-4-ylamino)-3-hydroxy-1-phenylbutan-2-yl)-5-oxo-3,4,5,6-tetrahydro-2H-benzo[b][1,4]oxazocine-10-carboxamide | 597.752 | 598.3 |
| 33 | tert-butyl 2-(3-(((2S,3R)-4-((S)-6-ethyl-2,2-spirocyclopentylchroman-4-ylamino)-3-hydroxy-1-phenylbutan-2-yl)carbamoyl)phenyl) pyrrolidine-1-carboxylate | 667.886 | 668.4 |
| 34 | N-((2S,3R)-4-((S)-6-ethyl-2,2-spirocyclopentylchroman-4-ylamino)-3-hydroxy-1-phenylbutan-2-yl)-3-(pyrrolidin-2-yl)benzamide | 567.769 | 568.3 |
| 35 | N-((2S,3R)-4-((S)-6-ethyl-2,2-spirocyclobutylchroman-4-ylamino)-3-hydroxy-1-phenylbutan-2-yl)-2-methoxy-5-(2-oxopyrrolidin-1-yl)benzamide | 597.752 | 598.2 |
| 36 | N-((2S,3R)-4-((S)-6-ethyl-2,2spirocyclobutylchroman-4-ylamino)-3-hydroxy-1-phenylbutan-2-yl)-2-fluoro-3-(2-oxopyrrolidin-1-yl)benzamide | 585.716 | 586.2 |
| 37 | N-((1S,2R)-3-(((2R,4S)-6-ethyl-3,4,4',5'-tetrahydrospiro[chromene-2,3'-furan]-4-yl)amino)-2-hydroxy-1-(phenylmethyl)propyl)-4-fluoro-3-(2-oxo-1-pyrrolidinyl)benzamide | 1203.43 | 602.2 |
| 38 | N-((1S,2R)-3-(((2R,4S)-6-ethyl-3,4,4',5'-tetrahydrospiro[chromene-2,3'-furan]-4-yl)amino)-2-hydroxy-1-(phenylmethyl)propyl)-2-fluoro-3-(2-oxo-1-pyrrolidinyl)benzamide | 1203.43 | 602.2 |
| 39 | N-((1S,2R)-1-((3-cyanophenyl)methyl)-3-3-(((4S)-6-ethyl-,4-dihydrospiro[chromene-2,1'-cyclobutan]-4-yl)amino)-2-hydroxypropyl)-2-fluoro-3-(2-oxo-1-pyrrolidinyl)benzamide | 610.7261 | 611 |
| 40 | N-((1S,2R)-3-(((1S)-3,3-dimethyl-7-(methyloxy)-4-oxo-1,2,3,4-tetrahydro-1-naphthalenyl)amino)-2-hydroxy-1-(phenyl-methyl)propyl)-2-fluoro-3-(2-oxo-1-pyrrolidinyl)benzamide | 1175.3764 | 588 |
| 41 | N-((1S,2R)-3-(((1S)-3,3-dimethyl-7-(methyloxy)-4-oxo-1,2,3,4-tetrahydro-1-naphthalenyl)amino)-2-hydroxy-1-(phenylmethyl)propyl)-3-(1,1-dioxido-1,2-thiazinan-2-yl)-2-fluoro-5-((1-methylethyl)amino)benzamide | 1389.7286 | 695 |
| 42 | N-((2S,3R)-4-((S)-3,4-dihydro-2,2-spirocyclopentyl-thiochroman-4-ylamino)-3-hydroxy-1-phenylbutan-2-yl)-2-(3-methyl-piperidin-1-yl)isonicotinamide | 584.825 | 585 |
| 43 | N-((1S,2R)-3-(((3R,4'S)-6'-(2,2-dimethyl-propyl)-3',4,4',5-tetrahydrospiro[furan-3,2'-pyrano[2,3-b]pyridin]-4'-yl)amino)-2-hydroxy-1-(phenylmethyl)propyl)-4-fluoro-3-(2-oxo-1-pyrrolidinyl)benzamide | 1289.567 | 645 |
| 44 | 3-fluoro-N-((2S,3R)-3-hydroxy-4-((S)-6-neopentyl-3,4-dihydro-2,2-spirocyclo-tetrahydrofuranyl-pyrano[2,3-b]pyridin-4-ylamino)-1-phenylbutan-2-yl)picolinamide | 1125.3642 | 563 |
| 45 | 2-chloro-N-((2S,3R)-4-((S)-6-ethyl-2,2-spirocyclohexylchroman-4-ylamino)-3-hydroxy-1-phenylbutan-2-yl)-6-(5-hydroxypentanamido) isonicotinamide | 663.254 | 663 |
| 46 | N-((2S,3R)-4-((S)-6-ethyl-2,2-spirocyclopentylchroman-4-ylamino)-3-hydroxy-1-phenylbutan-2-yl)-2-isobutylquinoline-4-carboxamide | 605.818 | 606 |
| 47 | N-((1S,2R)-3-(((4S)-6-ethyl-2,2-dimethyl-3,4-dihydro-2H-chromen-4-yl)amino)-2-hydroxy-1-(phenylmethyl)propyl)-2-fluorobenzamide | 490.616 | 491 |
| 48 | N-((2S,3R)-3-(((4S)-6-ethyl-2,2-dimethyl-3,4-dihydro-2H-chromen-4-yl)amino)-2-hydroxy-1-(phenylmethyl)propyl)benzamide | 472.625 | 473 |
| 49 | N-((2S,3R)-4-((S)-6-ethyl-2,2-spirocyclobutylchroman-4-ylamino)-3-hydroxy-1-phenylbutan-2-yl)-4-fluorobenzamide | 502.626 | 503 |

-continued

| Ex. No. | Name | MW | Mass Found |
|---|---|---|---|
| 50 | N-((1S,2R)-3-(((4S)-6-ethyl-3,4-dihydro-2spiro[chromene-,1'-cyclobutan]-4-yl)amino)-2-hydroxy-1-(phenylmethyl)propyl)-4-fluoro-3-(2-pyridinyl)benzamide | 579.7122 | 580 |
| 51 | N-((1S,2R)-3-(((4S)-6-ethyl-3,4-dihydro-spiro[chromene-2,1'-cyclobutan]-4-yl)amino)-2-hydroxy-1-(phenylmethyl)propyl)-2-(2-fluorophenyl)-4-pyridine-carboxamide | 579.7122 | 580 |
| 52 | 2-(2,6-difluorophenyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-4-pyridinecarboxamide | 597.7023 | 598 |
| 53 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-1-((1R)-1-phenylethyl)-1H-benzimidazole-6-carboxamide | 671.8811 | 671.3 |
| 54 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-1-(phenylmethyl)-1H-benzimidazole-6-carboxamide | 657.8543 | 658.3 |
| 55 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-1-(2-phenylethyl)-1H-benzimidazole-6-carboxamide | 671.8811 | 672.2 |
| 56 | 4-bromo-N-((1S,2R)-3-(((4'S)-6'-bromo-3',4'-dihydrospiro[cyclobutane-1,2'-pyrano[2,3-b]pyridin]-4'-yl)amino)-2-hydroxy-1-(phenylmethyl)propyl)-1-(2-phenylethyl)-1H-indole-6-carboxamide | 758.5512 | 759.2 |
| 57 | N-((1S,2R)-3-(((4'S)-6'-bromo-3',4'-dihydrospiro[cyclobutane-1,2'-pyrano[2,3-b]pyridin]-4'-yl)amino)-2-hydroxy-1-(phenylmethyl)propyl)-4-(2-cyanophenyl)-1-(2-phenylethyl)-1H-indole-6-carboxamide | 780.7628 | 782.3 |
| 58 | N-((2S,3R)-4-((S)-6-ethyl-2,2-spirocyclo-pentylchroman-4-ylamino)-3-hydroxy-1-phenylbutan-2-yl)-4-fluoro-3-(2-oxopyrrolidin-1-yl)benzamide | 599.743 | 600 |
| 59 | (S)-3-(benzyloxy)-N-((2S,3R)-4-(6-ethyl-2,2-spirocyclopentyl-chroman-4-ylamino)-3-hydroxy-1-phenylbutan-2-yl)-2,3-dihydro-1H-indene-5-carboxamide | 644.851 | 645 |
| 60 | N-((1S,2R)-3-(6-ethyl-3,4-dihydrospiro[chromene-2,1'-cyclobutan]-4-yl)amino)-2-hydroxy-1-(phenylmethyl)propyl)-3-furancarboxamide | 474.598 | 475 |
| 61 | N-((1S,2R)-3-(((4S)-6-ethyl-3,4-dihydro-spiro[chromene-2,1'-cyclobutan]-4-yl)amino)-2-hydroxy-1-(phenylmethyl)propyl)benzenesulfonamide | 520.69 | 521 |
| 62 | 4-fluoro-N-((1S,2R)-2-hydroxy-1-(phenyl-methyl)-3-(((4S)-6-((trifluoromethyl)oxy)-3,4-dihydrospiro[chromene-2,1'-cyclo-butan]-4-yl)amino)propyl)-3-(2-oxo-1-pyrrolidinyl)benzamide | 641.659 | 642 |
| 63 | N-((1S,2R)-2-hydroxy-1-(phenylmethyl)-3-(((4S)-6-((trifluoromethyl)oxy)-3,4-dihydrospiro[chromene-2,1'-cyclobutan]-4-yl)amino)propyl)-5-isoxazole-carboxamide | 531.528 | 532 |
| 64 | N-((1S,2R)-3-(((4S)-6-ethyl-7-fluoro-3,4-dihydrospiro[chromene-2,1'-cyclobutan]-4-yl)amino)-2-hydroxy-1-(phenylmethyl)propyl)-4-fluoro-3-(2-oxo-1-pyrrolidinyl)benzamide | 603.706 | 604 |
| 65 | N-((1S,2R)-3-(((4S)-6-ethyl-7-fluoro-3,4-dihydrospiro[chromene-2,1'-cyclobutan]-4-yl)amino)-2-hydroxy-1-(phenylmethyl)propyl)-5-isoxazolecarboxamide | 493.576 | 494 |
| 66 | N-((1S,2R)-3-(((4S)-6-ethyl-3,4-dihydro-spiro[chromene-2,1'-cyclobutan]-4-yl)amino)-2-hydroxy-1-(phenylmethyl)propyl)-2-pyrazinecarboxamide | 486.613 | 487 |
| 67 | N-((1S,2R)-3-(((4S)-6-acetyl-3,4-dihydro-spiro[chromene-2,1'-cyclobutan]-4-yl)amino)-2-hydroxy-1-(phenylmethyl)propyl)-4-fluoro-3-(2-oxo-1-pyrrolidinyl)benzamide | 599.6992 | 600 |
| 68 | N-((1S,2S)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-5-(methyl(methylsulfonyl)amino)-N'-((1R)-1-phenylethyl)-1,3-benzenedicarboxamide | 782.0135 | 782 |
| 69 | N-((1S,2S)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-2-fluoro-3-(2-oxo-1-pyrrolidinyl)benzamide | 628.7845 | 629 |
| 70 | N-((1S,2S)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-5-(1,1-dioxido-1,2-thiazinan-2-yl)-2-fluoro-3-((1-methylethyl)amino)benzamide | 735.9606 | 736 |
| 71 | N-((1S,2S)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-4-fluoro-3-(2-oxo-1-pyrrolidinyl)benzamide | 628.7845 | 629 |
| 72 | N-((1S,2R)-3-(((3S,4R)-6-bromo-3-hydroxy-2,2-dimethyl-3,4-dihydro-2H-chromen-4-yl)amino)-2-hydroxy-1-(phenylmethyl)propyl)-2-fluoro-3-(2-oxo-1-pyrrolidinyl)benzamide | 1281.093 | 641 |
| 73 | N-((1S,2R)-3-(((3R,4S)-6-bromo-3-hydroxy-2,2-dimethyl-3,4-dihydro-2H-chromen-4-yl)amino)-2-hydroxy-1-(phenylmethyl)propyl)-3-(1,1-dioxido-1,2-thiazinan-2-yl)-2-fluoro-5-((1-methyl-ethyl)amino)benzamide | 1495.4452 | 749 |
| 74 | N-((1S,2R)-3-(((3R,4S)-6-bromo-3-hydroxy-2,2-dimethyl-3,4-dihydro-2H-chromen-4-yl)amino)-2-hydroxy-1-(phenylmethyl)propyl)-4-fluoro-3-(2-oxo-1-pyrrolidinyl)benzamide | 1281.093 | 642 |
| 75 | N-((1S,2R)-1-((3-cyanophenyl)methyl)-2-hydroxy-3-(((4S)-6-(4-morpholinyl)-3,4-dihydrospiro[chromene-2,1'-cyclobutan]-4-yl) amino)propyl)-2-fluoro-3-(2-oxo-1-pyrrolidinyl)benzamide | 667.7778 | 668 |
| 76 | N-((2S,3R)-4-((S)-6-ethyl-2,2-spirocyclo-pentylchroman-4-ylamino)-3-hydroxy-1-phenylbutan-2-yl)-4-carboxamide-(S)-methyl 2-(2,3,4,5-tetrahydro-5H-imidazole-[1,2-a]azepin-6-yl) acetate AND N-((2S,3R)-4-((S)-6-ehtyl-2,2-spiro-cyclo-pentylchroman-4-ylamino)-3-hydroxy-1-phenylbutan-2-yl)-4-carboxamide-(R)-methyl 2-(2,3,4,5-tetrahydro-5H-imidazole-[1,2-a]azepin-6-yl) acetate | 1353.71 | 676.7 |
| 77 | N-((1S,2R)-3-(((4S)-6-bromo-3,4-dihydro-spiro[chromene-2,1'-cyclobutan]-4-yl)amino)-2-hydroxy-1-(phenylmethyl)propyl)-1,8-naphthyridine-2-carboxamide | 587.5149 | 589 |
| 78 | N-((2S,3R)-4-((S)-6-ethyl-2,2-spirocyclo-hexylchroman-4-ylamino)-3-hydroxy-1-phenylbutan-2-yl)-2-(piperidin-1-yl)isonicotinamide | 596.811 | 597.3 |

| Ex. No. | Name | MW | Mass Found |
|---|---|---|---|
| 79 | N-((2S,3R)-4-((S)-6-ethyl-2,2-spirocycloheptylchroman-4-ylamino)-3-hydroxy-1-phenylbutan-2-yl)-2-(piperidin-1-yl)isonicotinamide | 610.838 | 611.3 |
| 80 | N-((2S,3R)-3-hydroxy-4-((S)-6-methyl-2,2-spirocyclopentylchroman-4-ylamino)-1-phenylbutan-2-yl)-2-(3-methylpiperidin-1-yl)isonicotinamide | 1165.57 | 583.3 |
| 81 | N-((2S,3R)-3-hydroxy-4-((S)-6-triflouromethoxy-2,2-spirocyclopentylchroman-4-ylamino)-1-phenylbutan-2-yl)-2-(3-methylpiperidin-1-yl)isonicotinamide | 1305.51 | |
| 82 | N-((2S,3R)-3-hydroxy-4-((S)-6-isopropyl-2,2-spirocyclopentylchroman-4-ylamino)-1-phenylbutan-2-yl)-2-(3-methylpiperidin-1-yl)isonicotinamide | 1221.68 | 611.3 |
| 83 | N-((2S,3R)-3-hydroxy-4-((S)-6-isopropyl-2,2-spirocyclopentylchroman-4-ylamino)-1-phenylbutan-2-yl)-2-methyl-6-(3-methyl-piperidin-1-yl)isonicotinamide | 1249.73 | 625.3 |
| 84 | N-((2S,3R)-3-hydroxy-4-((S)-6-isopropyl-2,2-spirocyclopentylchroman-4-ylamino)-1-phenylbutan-2-yl)-2-methoxy-6-(3-methylpiperidin-1-yl)isonicotinamide | 1281.73 | 641.3 |
| 85 | N-((2S,3R)-4-((S)-2,2-spirocyclopentyl-chroman-4-ylamino)-3-hydroxy-1-phenyl-butan-2-yl)-2-(3-methylpiperidin-1-yl)isonicotinamide | 1137.52 | 569.3 |
| 86 | N-((2S,3R)-4-((S)-2,2-spirocyclopentyl-chroman-4-ylamino)-3-hydroxy-1-phenyl-butan-2-yl)-4-fluoro-3-(2-oxopyrrolidin-1-yl)benzamide | 571.689 | 572 |
| 87 | 6-(cyclopentyloxy)-N-((2S,3R)-4-((S)-6-ethyl-2,2-spirocyclobutyl-chroman-4-ylamino)-3-hydroxy-1-phenylbutan-2-yl)pyridazine-3-carboxamide | 570.73 | 571 |
| 88 | N-((2S,3R)-4-((S)-2,2-spirocyclobutyl-chroman-4-ylamino)-3-hydroxy-1-phenyl-butan-2-yl)-2-(3-methylpiperidin-1-yl)isonicotinamide | 1109.46 | 555.3 |
| 89 | N-((2S,3R)-4-((S)-2,2-spirocyclobutyl-chroman-4-ylamino)-3-hydroxy-1-phenyl-butan-2-yl)-4-fluoro-3-(2-oxopyrrolidin-1-yl) benzamide | 557.662 | 558 |
| 90 | N-((1S,2R)-3-(((4S)-6-bromo-3,4-dihydro-spiro[chromene-2,1'-cyclobutan]-4-yl)amino)-2-hydroxy-1-(phenylmethyl)propyl)-4-fluoro-3-(2-oxo-1-pyrrolidinyl)benzamide | 636.558 | 631.1; 638.1 |
| 91 | N-((1S,2R)-3-(((4S)-6-bromo-3,4-dihydro-spiro[chromene-2,1'-cyclobutan]-4-yl)amino)-2-hydroxy-1-(phenylmethyl)propyl)-2-((3S)-3-methyl-1-piperidinyl)-4-pyridinecarboxamide | 1267.25 | 633.2; 635.1 |
| 92 | N-((1S,2R)-3-(((4'R)-3',4'-dihydrospiro[cyclobutane-1,2'-pyrano[2,3-c]pyridin]-4'-ylamino)-2-hydroxy-1-(phenylmethyl)propyl)-4-fluoro-3-(2-oxo-1-pyrrolidinyl)benzamide | 558.651 | 559.3 |
| 93 | N-((1S,2R)-3-(((4'S)-3',4'-dihydrospiro[cyclobutane-1,2'-pyrano[2,3-c]pyridin]-4'-ylamino)-2-hydroxy-1-(phenylmethyl)propyl)-4-fluoro-3-(2-oxo-1-pyrrolidinyl)benzamide | 558.651 | 559.3 |
| 94 | N-((2S,3R)-4-((S)-2,2-spirocyclobutyl-3,4-dihydro-2H-pyrano[2,3-c]pyridin-4-ylamino)-3-hydroxy-1-phenylbutan-2-yl)-4-fluoro-3-(2-oxopyrrolidin-1-yl)benzamide | 593.096 | 593.1 |
| 95 | 6-chloro-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-3-fluoro-2-pyridinecarboxamide | 581.1282 | 581.2 |
| 96 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-3-fluoro-2-pyridinecarboxamide | 546.6831 | 547.2 |
| 97 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-3-fluoro-2-pyridinecarboxamide | 504.6027 | 505.2 |
| 98 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-3-fluoro-4-pyridinecarboxamide | 546.6831 | 547.2 |
| 99 | 5-chloro-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-fluorobenzamide | 580.1401 | 580.2 |
| 100 | N-((1S,2R)-3-(((4'S)-6'-(2,2-dimethyl-propyl)-3',4'-dihydrospiro[cyclobutane-1,2'-pyrano[2,3-b]pyridin]-4'-yl)amino)-2-hydroxy-1-(phenylmethyl)propyl)-2-fluoro-5-(trifluoromethyl)benzamide | 613.6921 | 614.2 |
| 101 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-2-fluoro-3-(2-oxo-1-pyrrolidinyl)benzamide | 586.7041 | 587.3 |
| 102 | N-((1S,2R)-3-(((4'S)-6'-ethyl-3',4'-dihydrospiro[cyclobutane-1,2'-pyrano[2,3-b]pyridin]-4'-yl)amino)-2-hydroxy-1-(phenylmethyl)propyl)-4-fluoro-3-(2-oxo-1-pyrrolidinyl)benzamide | 586.7041 | 587.3 |
| 103 | N-((1S,2R)-3-(((1S)-3,3-dimethyl-7-((3S)-tetrahydro-3-furanyloxy)-1,2,3,4-tetra-hydro-1-naphthalenyl)amino)-2-hydroxy-1-(phenylmethyl)propyl)-4-fluoro-3-(2-oxo-1-pyrrolidinyl)benzamide | 629.7686 | 630.3 |
| 104 | N-((1S,2R)-3-(((1S)-3,3-dimethyl-7-((3S)-tetrahydro-3-furanyloxy)-1,2,3,4-tetra-hydro-1-naphthalenyl)amino)-2-hydroxy-1-(phenylmethyl)propyl)-2-fluoro-3-(2-oxo-1-pyrrolidinyl)benzamide | 629.7686 | 630.3 |
| 105 | N-((2S,3R)-4-((S)-6,8-difluoro-3,4-dihydrospiro[chromene-2,1'-cyclopentan]-4-yl)amino)-3-hydroxy-1-phenylbutan-2-yl)-2-((+/−)-3-methylpiperidin-1-yl)isonicotinamide | 1209.48 | 605 |
| 106 | N-((2S,3R)-4-((S)-6-ethyl-3,4-dihydro-spiro[chromene-2,1'-cyclopentan]-4-yl)amino)-3-hydroxy-1-phenylbutan-2-yl)-3-(pyridin-2-yl)benzamide | 575.749 | 576 |
| 107 | N-((2S,3R)-4-((S)-6-fluoro-3,4-dihydro-spiro[chromene-2,1'-cyclopentan]-4-yl)amino)-3-hydroxy-1-phenylbutan-2-yl)-2-(3-methylpiperidin-1-yl)isonicotinamide | 1173.5 | 587 |
| 108 | N-((2S,3R)-4-((S)-6-fluoro-3,4-dihydro-spiro[chromene-2,1'-cyclopentan]-4-yl)amino)-3-hydroxy-1-phenylbutan-2-yl)-2-(piperidin-1-yl)isonicotinamide | 572.721 | 573 |
| 109 | N-((2S,3R)-4-((S)-6,8-difluoro-3,4-di-hydrospiro[chromene-2,1'-cyclopentan]-4-yl)amino)-3-hydroxy-1-phenylbutan-2-yl)-2-(piperidin-1-yl)isonicotinamide | 590.711 | 591 |
| 110 | N-((2S,3R)-4-((S)-6-ethyl-3,4-dihydro-spiro[chromene-2,1'-cyclobutyl])-3-hydroxy-1-phenylbutan-2-yl)-2-methoxy-6-(3-methylpiperidin-1-yl)isonicotinamide | 1225.62 | 613 |
| 111 | N-((2S,3R)-4-((S)-6-ethyl-3,4-dihydro-spiro[chromene-2,1'-cyclobutyl])-3-hydroxy-1-phenylbutan-2-yl)-6-(3-methylpiperidin-1-yl)isonicotinamide | 1165.57 | 583 |
| 112 | N-((2S,3R)-4-((S)-6-ethyl-3,4-dihydro-spiro[chromene-2,1'-cyclobutyl) | 1193.62 | 597 |

-continued

| Ex. No. | Name | MW | Mass Found |
|---|---|---|---|
| 113 | N-((1S,2R)-3-(((4S)-6-bromo-3,4-dihydro-spiro[chromene-2,1'-cyclopentan]-4-yl)amino)-2-hydroxy-1-(phenylmethyl)propyl)-2-methyl-6-((3R)-3-methyl-1-piperidinyl)-4-pyridinecarboxamide | 1323.36 | 662 |
| 114 | N-((1S,2R)-3-(((4S)-6-bromo-3,4-dihydro-spiro[chromene-2,1'-cyclopentan]-4-yl)amino)-2-hydroxy-1-(phenylmethyl)propyl)-2-(methyloxy)-6-((3R)-3-methyl-1-piperidinyl)-4-pyridinecarboxamide | 1355.36 | 678 |
| 115 | N-((1S,2R)-3-(((4S)-6-ethyl-3,4-dihydro-spiro[chromene-2,1'-cyclobutan]-4-yl)amino)-2-hydroxy-1-(phenylmethyl)propyl)-4-fluoro-3-(2-oxo-1-pyrrolidinyl)benzamide | 585.716 | 586 |
| 116 | N-((2S,3R)-4-((S)-6-neopenyl-3,4-dihydrospiro[chromene-2,1'-cyclopentan]-4-yl)amino)-3-hydroxy-1-phenylbutan-2-yl)-4-fluoro-3-(2-oxopyrrolidin-1-yl)benzamide | 641.823 | 642 |
| 117 | N-((2S,3R)-4-((S)-6-neopentyl-3,4-dihydrospiro[chromene-2,1'-cyclopentan]-4-yl)amino)-3-hydroxy-1-phenylbutan-2-yl)-2-(3-methylpiperidin-1-yl)isonicotinamide | 1277.78 | 639 |
| 118 | 4-fluoro-N-((1S,2R)-3-(((4S)-6-fluoro-3,4-dihydrospiro[chromene-2,1'-cyclobutan]-4-yl)amino)-2-hydroxy-1-(phenylmethyl)propyl)-3-(2-oxo-1-pyrrolidinyl)benzamide | 575.653 | 576 |
| 119 | N-((1S,2R)-3-(((4S)-6-fluoro-3,4-dihydro-spiro[chromene-2,1'-cyclobutan]-4-yl)amino)-2-hydroxy-1-(phenylmethyl)propyl)-2-(3-methyl-1-piperidinyl)-4-pyridinecarboxamide | 572.721 | 573 |
| 120 | N-((1S,2R)-3-(((4S)-6-(2,2-dimethyl-propyl)-3,4-dihydrospiro[chromene-2,1'-cyclobutan]-4-yl)amino)-2-hydroxy-1-(phenylmethyl) propyl)-4-fluoro-3-(2-oxo-1-pyrrolidinyl) benzamide | 627.796 | 628 |
| 121 | 4-fluoro-N-((1S,2R)-2-hydroxy-1-(phenyl-methyl)-3-(((4S)-6-(trifluoromethyl)-3,4-dihydrospiro[chromene-2,1'-cyclobutan]-4-yl)amino)propyl)-3-(2-oxo-1-pyrrolidinyl)benzamide | 625.659 | 626 |
| 122 | 6-chloro-N-((1S,2R)-1-((3,5-difluoro-phenyl) methyl)-3-(((4'S)-6'-(2,2-dimethyl-propyl)-3',4'-dihydrospiro[cyclobutane-1,2'-pyrano[2,3-b]pyridin]-4'-yl)amino)-2-hydroxypropyl)-3-fluoro-2-pyridinecarboxamide | 617.1084 | 618 |
| 123 | 6-chloro-N-((1S,2R)-1-((3-cyanophenyl) methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3-fluoro-2-pyridinecarboxamide | 606.1383 | 607 |
| 124 | 6-chloro-N-((1S,2R)-3-(((4S)-6-chloro-7-(1-piperidinylmethyl)-3,4-dihydrospiro[chromene-2,1'-cyclobutan]-4-yl)amino)-2-hydroxy-1-(phenylmethyl)propyl)-3-fluoro-2-pyridinecarboxamide | 641.6111 | 642 |
| 125 | 2-fluoro-N-((1S,2R)-2-hydroxy-3-(((4S)-6-(4-morpholinyl)-3,4-dihydrospiro[chromene-2,1'-cyclobutan]-4-yl)amino)-1-(phenylmethyl) propyl)-3-(2-oxo-1-pyrrolidinyl)benzamide | 642.7677 | 643 |
| 126 | 4-fluoro-N-((1S,2R)-2-hydroxy-3-(((4S)-6-(4-morpholinyl)-3,4-dihydrospiro[chromene-2,1'-cyclobutan]-4-yl)amino)-1-(phenylmethyl) propyl)-3-(2-oxo-1-pyrrolidinyl)benzamide | 642.7677 | 643 |
| 127 | N-((2S,3R)-4-((S)-6-ethyl-2,2-spirocyclo-pentylchroman-4-ylamino)-3-hydroxy-1-phenylbutan-2-yl)-1-methyl-1H-pyrrole-2-carboxamide | 501.667 | 502 |
| 128 | N-((2S,3R)-4-((S)-6-ethyl-2,2-spirocyclo-pentylchroman-4-ylamino)-3-hydroxy-1-phenylbutan-2-yl)-5-methylisoxazole-4-carboxamide | 503.639 | 504 |
| 129 | N-((2S,3R)-4-((S)-6-ethyl-2,2-spirocyclo-pentylchroman-4-ylamino)-3-hydroxy-1-phenylbutan-2-yl)-5-(3-(trifluoromethyl)phenyl)furan-2-carboxamide | 632.719 | 633 |
| 130 | 5-bromo-N-((2S,3R)-4-((S)-6-ethyl-2,2-spirocyclopentylchroman-4-ylamino)-3-hydroxy-1-phenylbutan-2-yl)furan-2-carboxamide | 567.521 | 568 |
| 131 | N-((2S,3R)-4-((S)-6-ethyl-2,2-spirocyclo-pentylchroman-4-ylamino)-3-hydroxy-1-phenylbutan-2-yl)-1H-indole-2-carboxamide | 537.7 | 538 |
| 132 | N-((2S,3R)-4-((S)-6-ethyl-2,2-spirocyclo-pentylchroman-4-ylamino)-3-hydroxy-1-phenylbutan-2-yl)-1-methyl-1H-indole-2-carboxamide | 551.727 | 552 |
| 133 | N-((2S,3R)-4-((S)-6-ethyl-2,2-spirocyclo-pentylchroman-4-ylamino)-3-hydroxy-1-phenylbutan-2-yl)-5-methoxy-1H-indole-2-carboxamide | 567.726 | 568 |
| 134 | N-((2S,3R)-4-((S)-6-ethyl-2,2-spirocyclo-pentylchroman-4-ylamino)-3-hydroxy-1-phenylbutan-2-yl)-7-methoxybenzofuran-2-carboxamide | 568.71 | 569 |
| 135 | 5-bromo-N-((2S,3R)-4-((S)-6-ethyl-2,2-spirocyclopentylchroman-4-ylamino)-3-hydroxy-1-phenylbutan-2-yl)thiophene-2-carboxamide | 583.588 | 584 |
| 136 | N-((2S,3R)-4-((S)-6-ethyl-2,2-spirocyclo-pentylchroman-4-ylamino)-3-hydroxy-1-phenylbutan-2-yl)-5-methyl-1-phenyl-1H-pyrazole-4-carboxamide | 578.753 | 579 |
| 137 | N-((1S,2R)-3-(((4S)-6-ethyl-2,2-dimethyl-3,4-dihydro-2H-chromen-4-yl)amino)-2-hydroxy-1-(phenylmethyl)propyl)-4-fluoro-3-(2-oxo-1-pyrrolidinyl)benzamide | 573.705 | 574 |
| 138 | N-((1S,2R)-3-(((4S)-6-ethyl-2,2-dimethyl-3,4-dihydro-2H-chromen-4-yl)amino)-2-hydroxy-1-(phenylmethyl)propyl)-2-((3S)-3-methyl-1-piperidinyl)-4-pyridinecarboxamide and 'N-((1S,2R)-3-(((4S)-6-ethyl-2,2-dimethyl-3,4-dihydro-2H-chromen-4-yl)amino)-2-hydroxy-1-(phenylmethyl)propyl)-2-((3R)-3-methyl-1-piperidinyl)-4-pyridinecarboxamide | 1141.55 | 571 |
| 139 | 2-chloro-N-((1S,2R)-3-(((4S)-6-ethyl-2,2-dimethyl-3,4-dihydro-2H-chromen-4-yl) amino)-2-hydroxy-1-(phenylmethyl)propyl)-6-((3S)-3-methyl-1-piperidinyl)-4-pyridinecarboxamide and '2-chloro-N-((1S,2R)-3-(((4S)-6-ethyl-2,2-dimethyl-3,4-dihydro-2H-chromen-4-yl) amino)-2-hydroxy-1-(phenylmethyl)propyl)-6-((3R)-3-methyl-1-piperidinyl)-4-pyridinecarboxamide | 1210.44 | 605 |
| 140 | N-((1S,2R)-3-(((4S)-6-ethyl-2,2-dimethyl-3,4-dihydro-2H-chromen-4-yl)amino)-2-hydroxy-1-(phenylmethyl)propyl)-2-methyl-6-((3S)-3-methyl-1-piperidinyl)-4-pyridinecarboxamide and 'N-((1S,2R)-3-(((4S)-6-ethyl-2,2-dimethyl-3,4-dihydro-2H-chromen-4-yl)amino)-2-hydroxy-1-(phenylmethyl)propyl)-2-methyl-6-((3R)-3-methyl-1-piperidinyl)-4-pyridinecarboxamide | 1169.6 | 585 |
| 141 | N-((1S,2R)-3-(((4S)-6-ethyl-2,2-dimethyl-3,4-dihydro-2H-chromen-4-yl)amino)-2-hydroxy-1-(phenylmethyl)propyl)-2-fluoro-3-(2-oxo-1-pyrrolidinyl)benzamide | 573.705 | 574 |

-continued

| Ex. No. | Name | MW | Mass Found |
|---|---|---|---|
| 142 | N-((1S,2R)-3-(((4S)-6-ethyl-2,2-dimethyl-3,4-dihydro-2H-chromen-4-yl)amino)-2-hydroxy-1-(phenylmethyl)propyl)-2-(methyloxy)-6-((3R)-3-methyl-1-piperidinyl)-4-pyridinecarboxamide and 'N-((1S,2R)-3-(((4S)-6-ethyl-2,2-dimethyl-3,4-dihydro-2H-chromen-4-yl)amino)-2-hydroxy-1-(phenylmethyl)propyl)-2-(methyloxy)-6-((3S)-3-methyl-1-piperidinyl)-4-pyridinecarboxamide | 1201.6 | 601 |
| 143 | N-((1S,2R)-3-(((4S)-6-ethyl-2,2-dimethyl-3,4-dihydro-2H-chromen-4-yl)amino)-2-hydroxy-1-(phenylmethyl)propyl)-5-isoxazolecarboxamide | 463.575 | 464 |
| 144 | N-((2S,3R)-4-((S)-6-ethyl-2,2-spirocyclopentylchroman-4-ylamino)-3-hydroxy-1-phenylbutan-2-yl)-3,5-bis(trifluoromethyl)benzamide | 634.657 | 635.2 |
| 145 | N-((2S,3R)-4-((S)-6-ethyl-2,2-spirocyclopentylchroman-4-ylamino)-3-hydroxy-1-phenylbutan-2-yl)pyrimidine-2-carboxamide | 500.639 | 501.3 |
| 146 | N-((1S,2R)-1-((3,5-difluorophenyl)methyl)-2-hydroxy-3-(((5'S)-3'-methyl-5',8'-dihydro-6'H-spiro[cyclobutane-1,7'-quinolin]-5'-yl) amino)propyl)-3-fluoro-4-(2-oxo-1-pyrrolidinyl)benzamide | 606.6853 | 607.3 |
| 147 | 5-bromo-2-butyl-N-((1S,2R)-3-(((4S)-6-ethyl-3,4-dihydrospiro[chromene-2,1'-cyclopentan]-4-yl)amino)-2-hydroxy-1-(phenylmethyl) propyl)-1,3-benzoxazole-7-carboxamide | 674.676 | 674.3 |
| 148 | 6-(1-cyclohexen-1-yl)-N-((1S,2R)-3-(((4S)-6-ethyl-3,4-dihydrospiro[chromene-2,1'-cyclopentan]-4-yl)amino)-2-hydroxy-1-(phenylmethyl)propyl)-2,2'-bipyridine-4-carboxamide | 656.866 | 657.3 |
| 149 | 6-cyclohexyl-N-((1S,2R)-3-(((4S)-6-ethyl-3,4-dihydrospiro[chromene-2,1'-cyclopentan]-4-yl)amino)-2-hydroxy-1-(phenylmethyl) propyl)-2,2'-bipyridine-4-carboxamide | 658.882 | 659.3 |
| 150 | 6-cyclopentyl-N-((1S,2R)-3-(((4S)-6-ethyl-3,4-dihydrospiro[chromene-2,1'-cyclo-pentan]-4-yl)amino)-2-hydroxy-1-(phenyl-methyl) propyl)-2,2'-bipyridine-4-carboxamide | 644.855 | 645.2 |
| 151 | 2-cyclopentyl-N-((1S,2R)-3-(((4S)-6-ethyl-3,4-dihydrospiro[chromene-2,1'-cyclo-pentan]-4-yl)amino)-2-hydroxy-1-(phenylmethyl) propyl)-6-(1,3-thiazol-2-yl)-4-pyridinecarboxamide | 650.883 | 651 |
| 152 | 2-cyclopentyl-N-((2S,3R)-4-((S)-6-ethyl-2,2-spirocyclopentylchroman-4-ylamino)-3-hydroxy-1-phenylbutan-2-yl)-6-(thiophen-3-yl) isonicotinamide | 649.895 | 650.3 |
| 153 | 2-cyclopentyl-N-((2S,3R)-4-((S)-6-ethyl-2,2-spirocyclopentylchroman-4-ylamino)-3-hydroxy-1-phenylbutan-2-yl)-6-(1H-pyrazol-1-yl) isonicotinamide | 633.832 | 634.4 |
| 154 | 2-(2-cyano-1H-pyrrol-1-yl)-6-cyclopentyl-N-((2S,3R)-4-((S)-6-ethyl-2,2-spirocyclo-pentyl-chroman-4-ylamino)-3-hydroxy-1-phenylbutan-2-yl)isonicotinamide | 657.854 | 658 |
| 155 | 2-cyclopentyl-N-((1S,2R)-3-(((4S)-6-ethyl-3,4-dihydrospiro[chromene-2,1'-cyclo-pentan]-4-yl)amino)-2-hydroxy-1-(phenyl-methyl) propyl)-6-((2R)-1-(methyl-sulfonyl)-2-pyrrolidinyl)-4-pyridinecarboxamide | 1429.93 | 715 |
| 156 | 2-((2R)-1-acetyl-2-pyrrolidinyl)-6-cyclo-pentyl-N-((1S,2R)-3-(((4S)-6-ethyl-3,4-dihydrospiro[chromene-2,1'-cyclopentan]-4-yl)amino)-2-hydroxy-1-(phenylmethyl)propyl)-4-pyridinecarboxamide | 1357.83 | 679.2 |
| 157 | N-((1S,2R)-3-(((4S)-6-ethyl-3,4-dihydro-spiro[chromene-2,1'-cyclobutan]-4-yl)amino)-2-hydroxy-1-(phenylmethyl)propyl)-5-isoxazolecarboxamide | 475.586 | 476.2 |
| 158 | N-((2S,3R)-4-((S)-6-ethyl-2,2-spirocyclo-butylchroman-4-ylamino)-3-hydroxy-1-phenylbutan-2-yl)furan-3-carboxamide | 474.598 | 589.3 |
| 159 | 1-acetylpyrrolidin-2-yl)-N-((2S,3R)-4-((S)-6-ethyl-2,2-spirocyclobutylchroman-4-ylamino)-3-hydroxy-1-phenylbutan-2-yl)-6-pentylisonicotinamide | 1333.8 | 667.2 |
| 160 | N-((1S,2R)-3-(((4S)-6-bromo-3,4-dihydro-spiro[chromene-2,1'-cyclobutan]-4-yl)amino)-2-hydroxy-1-(phenylmethyl)propyl)-1,5-dimethyl-1H-pyrazole-3-carboxamide | 553.498 | 533 |
| 161 | N-((1S,2R)-3-(((4S)-6-bromo-3,4-dihydro-spiro[chromene-2,1'-cyclobutan]-4-yl)amino)-2-hydroxy-1-(phenylmethyl)propyl)-1,3-dimethyl-1H-pyrazole-5-carboxamide | 553.498 | 533 |
| 162 | N-((1S,2R)-3-(((4S)-6-bromo-3,4-dihydro-spiro[chromene-2,1'-cyclobutan]-4-yl)amino)-2-hydroxy-1-(phenylmethyl)propyl)-5-isoxazolecarboxamide | 526.428 | 526 |
| 163 | N-((2S,3R)-4-((S)-6-bromo-2,2-spiro-cyclo-butylchroman-4-ylamino)-3-hydroxy-1-phenylbutan-2-yl)-1-methyl-1H-imidazole-4-carboxamide | 539.471 | 539 |
| 164 | N-((1S,2R)-3-(((4S)-6-bromo-3,4-dihydro-spiro[chromene-2,1'-cyclobutan]-4-yl)amino)-2-hydroxy-1-(phenylmethyl)propyl)-1-methyl-1H-imidazole-2-carboxamide | 539.471 | 539 |
| 165 | 5-chloro-N-((2S,3R)-4-((S)-6-ethyl-2,2-spirocyclopentylchroman-4-ylamino)-3-hydroxy-1-phenylbutan-2-yl)-1H-indole-7-carboxamide | 572.145 | 572.3 |
| 166 | N-((2S,3R)-4-((S)-6-ethyl-2,2-spirocyclo-pentylchroman-4-ylamino)-3-hydroxy-1-phenylbutan-2-yl)-5-(1H-pyrazol-1-yl)-1H-indole-7-carboxamide | 603.763 | 604.3 |
| 167 | N-((2S,3R)-4-((S)-6-ethyl-2,2-spirocyclo-pentylchroman-4-ylamino)-3-hydroxy-1-phenylbutan-2-yl)-2-(piperidin-1-yl) isonicotinamide | 582.784 | 583.3 |
| 168 | N-((2S,3R)-4-((S)-6-ethyl-2,2-spiroclo-pentylchroman-4-ylamino)-3-hydroxy-1-phenylbutan-2-yl)-2-(pyrrolidin-1-yl) isonicotinamide | 568.758 | 569.3 |
| 169 | N-((2S,3R)-4-((S)-6-ethyl-2,2-spirocyclo-pentylchroman-4-ylamino)-3-hydroxy-1-phenylbutan-2-yl)-2-morpholinoisonicotinamide | 584.757 | 585.3 |
| 170 | 5-chloro-N-((2S,3R)-4-((S)-6-ethyl-2,2-spirocyclopentylchroman-4-ylamino)-3-hydroxy-1-phenylbutan-2-yl)-3-formyl-1H-indole-7-carboxamide | 600.155 | 600.2 |
| 171 | N-((2S,3R)-4-((S)-6-ethyl-2,2-spirocyclo-pentylchroman-4-ylamino)-3-hydroxy-1-phenylbutan-2-yl)-2,3-dihydrobenzofuran-7-carboxamide | 540.7 | 541.3 |
| 172 | 5-bromo-N-((2S,3R)-4-((S)-6-ethyl-2,2-spirocyclopentylchroman-4-ylamino)-3-hydroxy-1-phenylbutan-2-yl)-2,3-dihydro-benzofuran-7-carboxamide | 619.596 | 621.2 |
| 173 | N-((2S,3R)-4-((S)-6-ethyl-2,2-spirocyclo-pentylchroman-4-ylamino)-3-hydroxy-1-phenylbutan-2-yl)-2,2-dimethyl-2,3-dihydrobenzofuran-7-carboxamide | 568.754 | 569.4 |
| 174 | 2-(azepan-1-yl)-N-((2S,3R)-4-((S)-6-ethyl-2,2-spirocyclopentylchroman-4-ylamino)-3-hydroxy-1-phenylbutan-2-yl) isonicotinamide | 596.811 | 597.3 |

-continued

| Ex. No. | Name | MW | Mass Found |
|---|---|---|---|
| 175 | 2-chloro-N-((2S,3R)-4-((S)-6-ethyl-2,2-spirocyclopentylchroman-4-ylamino)-3-hydroxy-1-phenylbutan-2-yl)-6-(piperidin-1-yl)isonicotinamide | 617.229 | 617.4 |
| 176 | N-((2S,3R)-4-((S)-6-ethyl-2,2-spirocyclopentylchroman-4-ylamino)-3-hydroxy-1-phenylbutan-2-yl)-2-methoxy-6-(piperidin-1-yl)isonicotinamide | 612.81 | 613.4 |
| 177 | N-((2S,3R)-4-((S)-6-ethyl-2,2-spirocyclopentylchroman-4-ylamino)-3-hydroxy-1-phenylbutan-2-yl)-2-(3-methylpiperidin-1-yl)isonicotinamide | 596.811 | 597.3 |
| 178 | N-((2S,3R)-4-((S)-6-ethyl-2,2-spirocyclopentylchroman-4-ylamino)-3-hydroxy-1-phenylbutan-2-yl)-2-methoxy-6-(3-methyl-piperidin-1-yl)isonicotinamide | 1253.67 | 627.3 |
| 179 | 2-(3-benzylpyrrolidin-1-yl)-N-((2S,3R)-4-((S)-6-ethyl-2,2-spirocyclopentylchroman-4-ylamino)-3-hydroxy-1-phenylbutan-2-yl)-6-methoxyisonicotinamide | 1377.82 | 689.3 |
| 180 | N-((2S,3R)-4-((S)-6-ethyl-2,2-spirocyclopentylchroman-4-ylamino)-3-hydroxy-1-phenylbutan-2-yl)-2-methyl-6-(3-methyl-piperidin-1-yl)isonicotinamide | 1221.68 | 611.3 |
| 181 | N-((2S,3R)-4-((S)-6-ethyl-2,2-spirocyclopentylchroman-4-ylamino)-3-hydroxy-1-phenylbutan-2-yl)-2-methoxy-6-(3-(pyridin-2-yl)pyrrolidin-1-yl)isonicotinamide | 1351.74 | 676.3 |
| 182 | 2-chloro-N-((2S,3R)-4-((S)-6-ethyl-2,2-spirocyclopentylchroman-4-ylamino)-3-hydroxy-1-phenylbutan-2-yl)-6-methylisonicotinamide | 548.123 | 548.2 |
| 183 | N-((2S,3R)-4-((S)-6-ethyl-2,2-spirocyclopentylchroman-4-ylamino)-3-hydroxy-1-phenylbutan-2-yl)-2-methoxy-6-((R)-3-phenylpiperidin-1-yl)isonicotinamide | 688.908 | 689.3 |
| 184 | 2-chloro-N-((2S,3R)-4-((S)-6-ethyl-2,2-spirocyclopentylchroman-4-ylamino)-3-hydroxy-1-phenylbutan-2-yl)-6-(3-methyl-piperidin-1-yl)isonicotinamide | 1262.51 | 631.3 |
| 185 | N-((2S,3R)-4-((S)-6-ethyl-2,2-spirocyclopentylchroman-4-ylamino)-3-hydroxy-1-phenylbutan-2-yl)-2-(2-fluorophenyl)-6-(3-methylpiperidin-1-yl)isonicotinamide | 1381.8 | 691.3 |
| 186 | N-((2S,3R)-4-((S)-6-ethyl-2,2-spirocyclopentylchroman-4-ylamino)-3-hydroxy-1-phenylbutan-2-yl)-2-methyl-6-(4-methyl-piperidin-1-yl)isonicotinamide | 610.838 | 611.3 |
| 187 | 2-((4aR)-4a,8a-dimethyl-octahydroisoquinolin-2(1H)-yl)-N-((2S,3R)-4-((S)-6-ethyl-2,2-spirocyclopentylchroman-4-yl-amino)-3-hydroxy-1-phenylbutan-2-yl)-6-methylisonicotinamide | 1357.91 | 651.3 |
| 188 | 2-(3,4-dihydro-2(1H)-isoquinolinyl)-N-((1S,2R)-3-(((4S)-6-ethyl-3,4-dihydrospiro[chromene-2,1'-cyclopentan]-4-yl)amino)-2-hydroxy-1-(phenylmethyl)propyl)-6-methyl-4-pyridinecarboxamide | 644.855 | 645.3 |
| 189 | N-((1S,2R)-3-(((4S)-6-ethyl-3,4-dihydrospiro[chromene-2,1'-cyclopentan]-4-yl)amino)-2-hydroxy-1-(phenylmethyl)propyl)-2-methyl-6-(4-phenyl-1-piperidinyl)-4-pyridinecarboxamide | 672.909 | 673.3 |
| 190 | N-((2S,3R)-4-((S)-6-ethyl-2,2-spirocyclopentylchroman-4-ylamino)-3-hydroxy-1-phenylbutan-2-yl)-2-(4-methoxyphenyl)-6-(3-methylpiperidin-1-yl)isonicotinamide | 1405.87 | 703.3 |
| 191 | N-((2S,3R)-4-((S)-6-ethyl-2,2-spirocyclopentylchroman-4-ylamino)-3-hydroxy-1-phenylbutan-2-yl)-2-(4-fluorophenyl)-6-(3-methylpiperidin-1-yl)isonicotinamide | 1381.8 | 691.3 |
| 192 | N-((2S,3R)-4-((S)-6-ethyl-2,2-spirocyclopentylchroman-4-ylamino)-3-hydroxy-1-phenylbutan-2-yl)-2-(3-fluorophenyl)-6-(3-methylpiperidin-1-yl)isonicotinamide | 1381.8 | 691.4 |
| 193 | 2-(3,3-dimethyl-1-piperidinyl)-N-((1S,2R)-3-(((4S)-6-ethyl-3,4-dihydrospiro[chromene-2,1'-cyclopentan]-4-yl)amino)-2-hydroxy-1-(phenylmethyl)propyl)-6-methyl-4-pyridinecarboxamide | 624.865 | 625.4 |
| 194 | 2-chloro-N-((1S,2R)-3-(((4S)-6-ethyl-3,4-dihydrospiro[chromene-2,1'-cyclopentan]-4-yl)amino)-2-hydroxy-1-(phenylmethyl)propyl)-6-((3S)-3-(2-hydroxyethyl)-1-piperidinyl)-4-pyridinecarboxamide | 1322.56 | 661.3 |
| 195 | 2-chloro-N-((2S,3R)-4-((S)-6-ethyl-2,2-spirocyclopentylchroman-4-ylamino)-3-hydroxy-1-phenylbutan-2-yl)-6-(2-methyl-piperidin-1-yl)isonicotinamide | 1262.51 | 631.3 |
| 196 | 2-chloro-N-((1S,2R)-3-(((4S)-6-ethyl-3,4-dihydrospiro[chromene-2,1'-cyclopentan]-4-yl)amino)-2-hydroxy-1-(phenylmethyl)propyl)-6-((3R)-3-(trifluoromethyl)-1-piperidinyl)-4-pyridinecarboxamide | 1370.45 | 685.3 |
| 197 | 2-chloro-N-((1S,2R)-3-(((4S)-6-ethyl-3,4-dihydrospiro[chromene-2,1'-cyclopentan]-4-yl)amino)-2-hydroxy-1-(phenylmethyl)propyl)-6-((3R)-3-fluoro-1-piperidinyl)-4-pyridinecarboxamide | 1270.44 | 635.3 |
| 198 | N-((1S,2R)-3-(((4S)-6-ethyl-3,4-dihydrospiro[chromene-2,1'-cyclobutan]-4-yl)amino)-2-hydroxy-1-(phenylmethyl)propyl)-3-methylbenzamide | 498.6632 | 499 |
| 199 | 2-chloro-N-((2S,3R)-4-((S)-6-ethyl-2,2-spirocyclopentylchroman-4-ylamino)-3-hydroxy-1-phenylbutan-2-yl)-6-(pyrrolidin-1-yl)isonicotinamide | 603.203 | 603 |
| 200 | N-((1S,2R)-3-(((4S)-6-ethyl-3,4-dihydrospiro[chromene-2,1'-cyclobutan]-4-yl)amino)-2-hydroxy-1-(phenylmethyl)propyl)-6-fluoro-1H-indazole-3-carboxamide | 542.6515 | 543 |
| 201 | N-((1S,2R)-3-(((4S)-6-ethyl-3,4-dihydrospiro[chromene-2,1'-cyclobutan]-4-yl)amino)-2-hydroxy-1-(phenylmethyl)propyl)-5-(2-fluorophenyl)-2-furancarboxamide | 568.6853 | 569 |
| 202 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-furanyl)-4-quinolinecarboxamide | 601.7431 | 602 |
| 203 | 5-((1,1-dimethylethyl)sulfonyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-thiophenecarboxamide | 610.8358 | 611 |
| 204 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-pyridinyl)-4-quinolinecarboxamide | 612.77 | 613 |
| 205 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-thienyl)-4-quinolinecarboxamide | 617.8101 | 618 |
| 206 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-(methyloxy)phenyl)-4-quinoline-carboxamide | 641.8077 | 642 |
| 207 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-((1-methylethyl)oxy)phenyl)-4-quinolinecarboxamide | 669.8613 | 670 |
| 208 | N-((1S,2R)-3-(((4S)-6-ethyl-3,4-dihydrospiro[chromene-2,1'-cyclobutan]-4-yl)amino)-2-hydroxy-1-(phenylmethyl)propyl)-2'-fluoro-3-biphenylcarboxamide | 578.7241 | 579 |

| Ex. No. | Name | MW | Mass Found |
|---|---|---|---|
| 209 | N-((1S,2R)-3-(((4S)-6-ethyl-3,4-dihydro-spiro[chromene-2,1'-cyclobutan]-4-yl)amino)-2-hydroxy-1-(phenylmethyl)propyl)-2-(2-(ethyloxy)phenyl)-4-quinolinecarboxamide | 655.8345 | 656 |

The following compounds in Tables 1 and 2 are additional representative es of Formulas I-III, as provided by the present invention.

TABLE 1

| Ex. No. | $R^1$ | B | $R^3$ and $R^4$ | $X^1$ | S |
|---|---|---|---|---|---|
| 210 | 1-pyridinyl- | benzyl-O— | H | NH | cyclobutyl |
| 211 | 2-pyridinyl- | benzyl-S— | H | S | cyclobutyl |
| 212 | 3-pyridinyl- | benzyl-NH— | H | O | cyclobutyl |
| 213 | pyrimidinyl- | benzyl-O— | H | NH | cyclopentyl |
| 214 | pyrimidinyl- | benzyl-S— | H | S | cyclopentyl |
| 215 | pyrimidinyl- | benzyl-NH— | H | O | cyclopentyl |
| 216 | pyrimidinyl- | Benzyl-CH$_2$— | H | SO$_2$ | cyclopropyl |
| 217 | tetrazolyl- | benzyl-O— | H | NH | cyclopropyl |
| 218 | tetrazolyl- | benzyl-S— | H | S | cyclopropyl |
| 219 | tetrazolyl- | benzyl-NH— | H | O | cyclohexyl |
| 220 | tetrazolyl- | benzyl-CH$_2$— | H | SO$_2$ | cyclohexyl |
| 221 | thiadiazolyl- | benzyl-O— | H | NH | cyclobutyl |
| 222 | thiadiazolyl- | benzyl-S— | H | S | cyclobutyl |
| 223 | thiadiazolyl- | benzyl-NH— | H | O | cyclobutyl |
| 224 | thiadiazolyl- | benzyl-CH$_2$— | H | SO$_2$ | cyclobutyl |
| 225 | benzimidazolyl- | benzyl-O— | H | NH | cyclopentyl |
| 226 | benzimidazolyl- | benzyl-S— | H | S | cyclopentyl |
| 227 | benzimidazolyl- | benzyl-NH— | H | O | cyclopentyl |
| 228 | benzimidazolyl- | benzyl-CH$_2$— | H | SO$_2$ | cyclohexyl |
| 229 | indolyl- | 4-CH$_3$-phenyl | H | NH | cyclohexyl |
| 230 | indolyl- | phenyl | H | S | cyclohexyl |

TABLE 2

| Ex. No. | $R^1$ | B | $R^3$ and $R^4$ | $X^1$ | S |
|---|---|---|---|---|---|
| 231 | 1-pyridinyl- | 4-CH$_3$-phenyl | H | NH | cyclobutyl |
| 232 | 2-pyridinyl- | 4-CH$_3$-phenyl | H | S | cyclobutyl |
| 233 | 3-pyridinyl- | 4-CH$_3$-pyridyl | H | O | cyclobutyl |
| 234 | pyrimidinyl- | 4-CH$_3$-phenyl | H | NH | cyclopentyl |
| 235 | pyrimidinyl- | 3-CH$_3$-phenyl | H | S | cyclopentyl |
| 236 | pyrimidinyl- | 3-CH$_3$-phenyl | H | O | cyclopentyl |
| 237 | pyrimidinyl- | 3-CH$_3$-phenyl | H | SO$_2$ | cyclopropyl |
| 238 | tetrazolyl- | 3-CH$_3$-phenyl | H | NH | cyclopropyl |
| 239 | tetrazolyl- | phenyl | H | S | cyclopropyl |
| 240 | tetrazolyl- | phenyl | H | O | cyclohexyl |
| 241 | tetrazolyl- | phenyl | H | SO$_2$ | cyclohexyl |
| 242 | thiadiazolyl- | phenyl | H | NH | cyclohexyl |
| 243 | thiadiazolyl- | pyridyl | H | S | cyclobutyl |
| 244 | thiadiazolyl- | phenyl | H | O | cyclobutyl |
| 245 | thiadiazolyl- | 3-F-phenyl | H | SO$_2$ | cyclobutyl |
| 246 | benzimidazolyl- | 3-Cl-phenyl | H | NH | cyclopentyl |
| 247 | benzimidazolyl- | 3-CN-phenyl | H | S | cyclopentyl |
| 248 | benzimidazolyl- | 3-NH$_2$-phenyl | H | O | cyclopentyl |
| 249 | benzimidazolyl- | 2-F-phenyl | H | SO$_2$ | cyclohexyl |
| 250 | indolyl- | 4-CH$_3$-phenyl | H | NH | cyclohexyl |
| 251 | indolyl- | phenyl | H | S | cyclohexyl |

The following examples were prepared by a method analogous to those described in Examples 1-4 above.

| Ex. No. | Compound Name | Mass Found |
|---|---|---|
| 252 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-fluorobenzamide | 564 |
| 253 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-pyridinecarboxamide | 547 |
| 254 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3-methyl-2-pyridinecarboxamide | 561 |
| 255 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-5-isoxazolecarboxamide | 537 |
| 256 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3-fluoro-2-pyridinecarboxamide | 565 |
| 257 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-((trifluoromethyl)oxy)benzamide | 630 |

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The specialist knows, or can easily establish, which protecting groups are suitable with the reactions described herein. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For example, the $R^{12}$ substituent is drawn unattached to any specific atom of ring $Z^2$, and therefore each of the n number of $R^{12}$ substituents may be attached to any atom of $Z^2$.

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I-III) vary with structural change, in general, activity possessed by compounds of Formulas I, II and III may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to modulate BACE activity.

In another embodiment of the invention, there is provided a method of making a compound of Formula I-III, the method comprising the step of reacting a compound 20

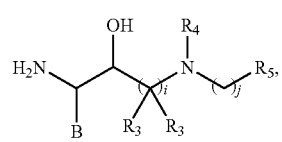

wherein i, j, A, B, $R^3$, $R^4$ and $R^5$ are as defined herein, with a compound having the structure $R^1$-W-X, wherein $R^1$ and W are as defined herein and X is a leaving group, to make a compound of Claim 1.

As appreciated by one or ordinary skill in the art, compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

The pharmacological properties and biological activity of the compounds of the invention (Formulas I-III) are shown by the following biological evaluations.

BIOLOGICAL EVALUATION

The following assays were used to characterize the ability of compounds of the invention to generally regulate the cleavage of amyloid beta precursor protein, thereby reducing or inhibiting the production of amyloid beta.

In Vitro Enzymatic BACE FRET (Fluorescence Resonance Energy Transfer) Assay

Assay buffer is 0.05 M acetate, pH 4.2, 10% DMSO final, 100 uM genapol (which is a nonionic detergent, below it's Critical Micelle Concentration). Enzyme (0.2 nM) is pre-incubated for one hour with inhibitors added in 1 uL of DMSO. Then the assay is started by the addition of FRET substrate (50 nM) and incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

The compounds of Examples 1-2, 5-41, 43-91, 93-107, 110-118, 120-126, 128-135, 136-143, 145-171 and 174-206 exhibited $IC_{50}$ values of 5 μM or less in the FRET in-vitro enzyme assay.

BACE Cell-Based Assay:

The cell-based assay measures inhibition or reduction of Aβ40 in conditioned medium of test compound treated APP containing cells.

Cells stably expressing Amyloid Precursor Protein (APP) were plated at a density of 40K cells/well in 96 well plates (Costar). The cells were cultivated for 24 h at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the compounds of Examples 1-2, 9-17, 19, 22-23, 25-27, 30, 34-41, 43-44, 47-48, 50-55, 58-59, 62-75, 78-83, 86-91, 93-104, 106, 110-113, 115-118, 120-126, 137-143, 146, 149-150, 154-157, 159, 162, 167, 169, 174-178, 183-184, 188, k 193-203, and 205-209 exhibited activities with $IC_{50}$ values of 5 μM or less in the HEK-293 cell-based assay.

Indications

Accordingly, compounds of the invention are useful for, but not limited to, the prevention or treatment of beta-secretase related diseases, including Alzheimer's disease. The compounds of the invention have the ability to modulate the formation of amyloid beta, and reduce the formation and deposition of plaque on the brain. In one embodiment of the invention, there is provided a method of treating a disorder related to a beta-secretase enzyme in a subject, the method comprising administering to the subject an effective dosage amount of a compound of Formulas I, II or III. In another embodiment, there is provided a method of reducing production of amyloid beta, and of reducing plaque formation. In yet another embodiment, there is provided a method of treating Alzheimer's disease.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrastemally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I, II or III with a pharmaceutically acceptable carrier to manufacture the medicament.

In yet another embodiment, there is provided a method of manufacturing a medicament for the treatment of Alzheimer's disease, the method comprising combining an amount of a compound according to Formulas I, II or III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

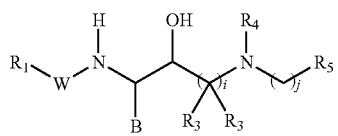

I or a stereoisomer, tautomer, or pharmaceutically acceptable salt, thereof, wherein $R^1$ is a fully unsaturated 5-6 membered monocyclic or 8-12 membered bicyclic, ring system, said ring system formed of carbon atoms and optionally including 1-3 heteroatoms if monocyclic or 1-6 heteroatoms if bicyclic, said heteroatoms selected from O, N, or S, wherein said ring system is optionally substituted independently with 1-5 substituents of oxo, $R^7$, $R^8$, $R^9$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

W is —C(=O)—, —OC(=O)—, —NHC(=O)—, —S(=O)$_b$— or —NHS(=O)$_b$—, wherein b is 1 or 2;

B is $R^2$—$(CR^{2a}R^{2a})_h$—, wherein $R^2$ is $C_1$-$C_{10}$ alkyl, $C_2$-$C_{10}$ alkenyl, $C_2$-$C_{10}$ alkynyl, or a ring selected from phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl wherein said $C_1$-$C_{10}$ alkyl, $C_2$-$C_{10}$ alkenyl, $C_2$-$C_{10}$ alkynyl and ring is optionally substituted independently with 1-5 substituents of $R^9$;

each $R^{2a}$, independently, is H, OH, NO$_2$, CN, NH$_2$, halo, $C_1$-$C_{10}$ alkyl, $C_1$-$C_{10}$ alkoxyl or haloalkyl; and h is 1;

i is 1;

j is 0;

each $R^3$, independently, is H, haloalkyl, CN, $C_{1\text{-}10}$-alkyl, or $C_{3\text{-}10}$-cycloalkyl;

$R^4$ is H, CN or $C_{1\text{-}10}$-alkyl;

$R^5$ is

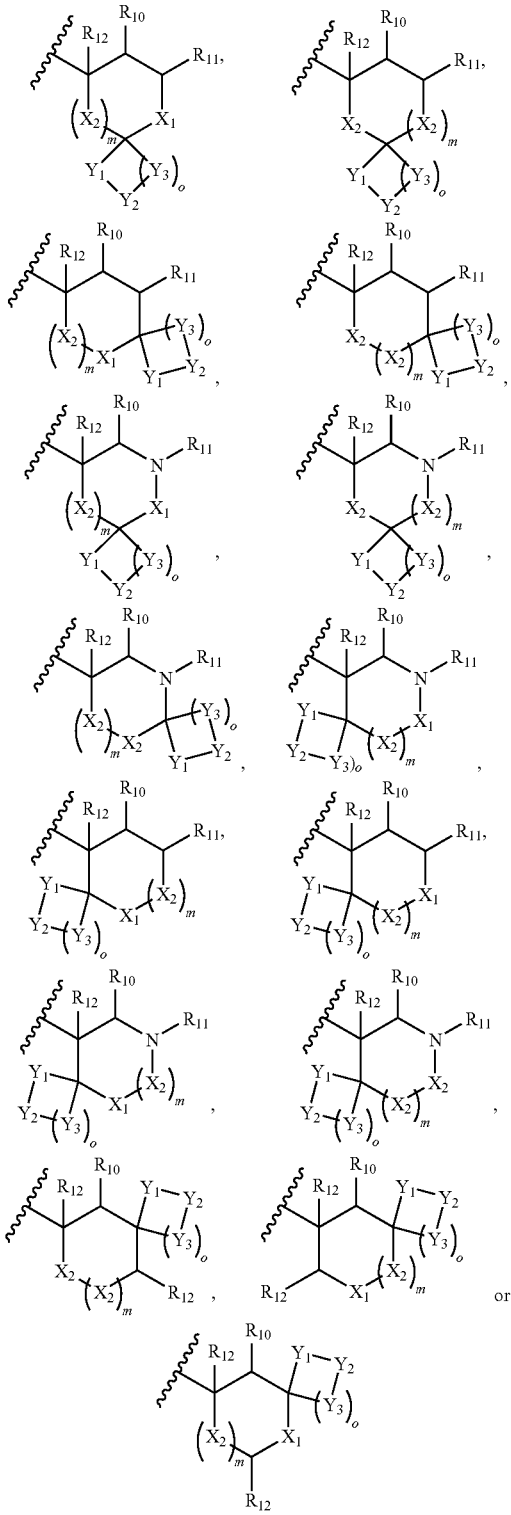

wherein $X^1$ is C(=O), O, S or $NR^{12}$;

each $X^2$, independently, is $CR^{12}R^{12}$;

each of $Y^1$, $Y^2$ and $Y^3$, independently, is $CR^{12}R^{12}$, O, S or $NR^{12}$;

m is 0, 1 or 2; and o is 0, 1, 2, 3, 4 or 5;

provided that (a) no more than two of $Y^1$, $Y^2$ and $Y^3$ is O, S or $NR^{12}$ and (b) when o is 0, then each of $Y^1$ and $Y^2$ is $CR^{12}R^{12}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{10}$ is H halo, haloalkyl, CN, OH, $NO_2$, $NH_2$, acetyl, $C_{1-10}$-alkyl, $C_{2-10}$-alkenyl, $C_{2-10}$ alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon or nitrogen atoms to which they are attached form a partially or fully saturated or unsaturated 5-6 membered second ring of carbon atoms optionally including 1-3 heteroatoms selected from O, N, or S, the second ring optionally substituted independently with 1-5 substituents of $R^{12}$, $R^{13}$, $R^{14}$ or $R^{15}$; and optionally fused to a 4-7 membered third ring, the third ring formed of carbon atoms optionally including 1-3 heteroatoms selected from O, N, or S, and optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl, phenyl or $R^{14}$;

$R^{13}$ is $NR^{14}R^{15}$, $NR^{15}R^{15}$, $OR^{14}$, $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

R[14] is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R[15]; and R[15] is H, halo, haloalkyl, CN, OH, NO$_2$, NH$_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, C$_{1-10}$-alkylamino-, C$_{1-10}$-dialkylamino-, C$_{1-10}$-thioalkoxyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

2. The compound of claim 1 wherein R$^1$ is an optionally substituted phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl or benzotriazolyl.

3. The compound of claim 1 wherein R$^1$ is

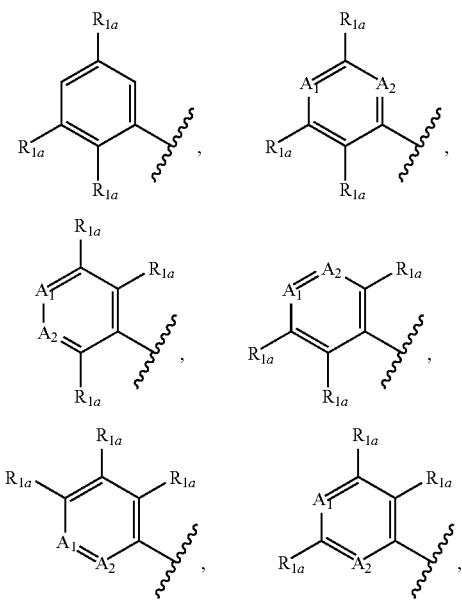

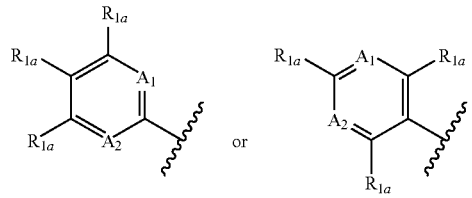

wherein
one of A$^1$ and A$^2$ is N and the other of A$^1$ and A$^2$ is CR$^{1a}$ or each of A$^1$ and A$^2$, independently, is N;

each R$^{1a}$, independently, is R$^7$, R$^8$, R$^9$, C(O)R$^7$, C(O)R$^8$, C(O)NR$^7$R$^7$, C(S)NR$^7$R$^7$, C(O)NR$^7$R$^8$, C(S)NR$^7$R$^8$, S(O)$_2$NR$^7$R$^7$, S(O)$_2$R$^8$, or S(O)$_2$NR$^7$R$^8$;

alternatively, two adjacent R$^{1a}$, s taken together with the carbon atoms to which they are attached form a partially or fully saturated or unsaturated 3-8 membered monocyclic ring, said ring formed of carbon atoms optionally including 1-3 heteroatoms selected from O, N, or S and optionally substituted independently with 1-3 substituents of oxo, R$^7$, R$^8$, R$^9$, NR$^7$R$^7$, NR$^7$R$^8$, OR$^7$, SR$^7$, OR$^8$, SR$^8$, C(O)R$^7$, OC(O)R$^7$, COOR$^7$, C(O)R$^8$, OC(O)R$^8$, COOR$^8$, C(O)NR$^7$R$^7$, C(S)NR$^7$R$^7$, NR$^7$C(O)R$^7$, NR$^7$C(S)R$^7$, NR$^7$C(O)NR$^7$R$^7$, NR$^7$C(S)NR$^7$R$^7$, NR$^7$(COOR$^7$), OC(O)NR$^7$R$^7$, C(O)NR$^7$R$^8$, C(S)NR$^7$R$^8$, NR$^7$C(O)R$^8$, NR$^7$C(S)R$^8$, NR$^7$C(O)NR$^7$R$^8$, NR$^7$C(S)NR$^7$R$^8$, NR$^7$(COOR$^8$), OC(O)NR$^7$R$^8$, S(O)$_2$NR$^7$R$^7$, NR$^7$S(O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$ or NR$^7$S(O)$_2$R$^8$.

4. The compound of claim 3 wherein at least one R$^{1a}$ substituent is an optionally substituted phenyl, naphthyl, pyridyl, pyrimidyl, pyridazinyl, pyrazinyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxo-pyrrolidinyl, oxo-imidazolidinyl, oxazolinyl, isoxazolinyl, thiazolinyl, pyrazolinyl, morpholinyl, piperidinyl, piperazinyl, pyranyl, oxo-pyranyl, dioxozinyl, cyclopropyl, cyclobutyl, cyclopentyl, cyclohexyl or cycloheptyl ring.

5. The compound of claim 1 wherein R$^5$ is

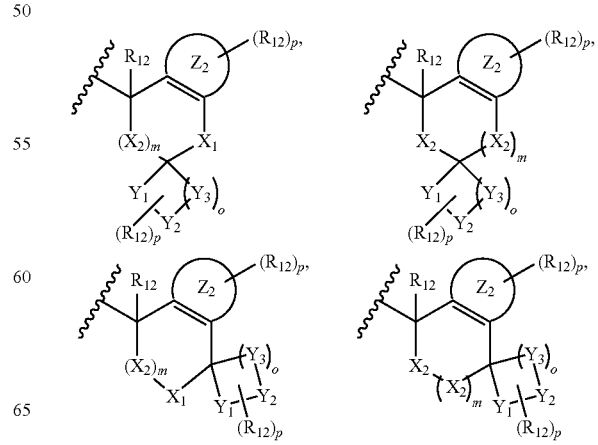

-continued

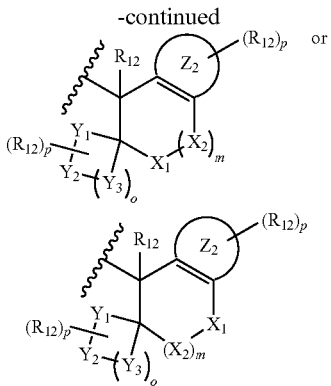

wherein
m, o, $R^{12}$, $X^1$, $X^2$, $Y^1$, $Y^2$ and $Y^3$ are as defined in claim 1;
wherein $R^{10}$ and $R^{11}$ taken together with the carbon atoms to which they are attached form a ring $Z^2$, said ring $Z^2$ is a partially saturated or fully unsaturated 5-8 membered monocyclic ring, formed of carbon atoms optionally including 1-3 heteroatoms selected from O, N, or S, provided that (a) no more than one of $Y^1$, $Y^2$ and $Y^3$ is O, S or $NR^{12}$ and (b) when o is 0, then each of $Y^1$ and $Y^2$ is $CR^{12}R^{12}$; and
each p, independently, is 0, 1, 2, 3, 4 or 5.

6. The compound of claim 5 wherein $Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring.

7. The compound of claim 1 wherein
each $R^3$, independently, is H, haloalkyl, CN or $C_{1-10}$-alkyl,
$R^4$ is H or $C_{1-10}$-alkyl; and
$R^5$ is

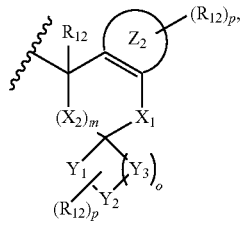

wherein m, o, $R^{12}$, $X^1$, $X^2$, $Y^1$, $Y^2$ and $Y^3$ are as defined in claim 1,
wherein $R^{10}$ and $R^{11}$ taken together with the carbon atoms to which they are attached form a ring $Z^2$, said ring $Z^2$ is an optionally substituted phenyl, pyridine, pyrimidine, triazine, pyridazine, pyrazine, pyrrole, imidazole, pyrazole, triazole, thiophene, thiazole, thiadiazole, isothiazole, furan, oxazole, oxadiazole or isoxazole ring, and
each p, independently, is 0, 1, 2, 3, 4 or 5.

8. A compound having a Formula II:

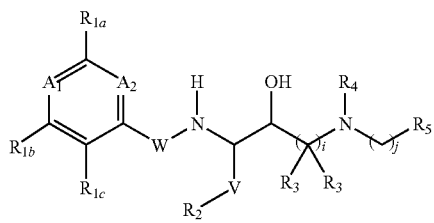

II or a stereoisomer, tautomer, or pharmaceutically acceptable salt, thereof, wherein
$A^1$ is N or $CR^{1a}$;
$A^2$ is N or $CR^{1c}$;
each $R^{1a}$, independently, is $R^7$, $R^8$, $R_9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;
$R^{1b}$ is $R^7$, $R^8$, $R_9$, $C(O)R^7$, $C(O)R^8$, $C(O)NR^7R^7$, $C(S)NR^7R^7$, $C(O)NR^7R^8$, $C(S)NR^7R^8$, $S(O)_2NR^7R^7$, $S(O)_2R^8$, or $S(O)_2NR^7R^8$;
each $R^{1c}$, independently, is H, haloalkyl, halo, CN, $C_{1-10}$-alkyl, $C_{2-10}$-alkenyl or $C_{2-10}$-alkynyl;
W is —C(=O)—, —OC(=O)O—, —NHC(=O)—, —S(=O)$_b$— or —NHS(=O)$_b$—, wherein b is 1 or 2;
V is —$(CR^{2a}R^{2a})_h$—, wherein each $R^{2a}$, independently, is H, $C_1$-$C_{10}$ alkyl or haloalkyl, and h is 1;
$R^2$ is phenyl optionally substituted independently with 1-3 substituents of
$R^3$ is H, haloalkyl, CN or $C_{1-10}$-alkyl;
$R^4$ is H, CN or $C_{1-10}$-alkyl;
$R^5$ is

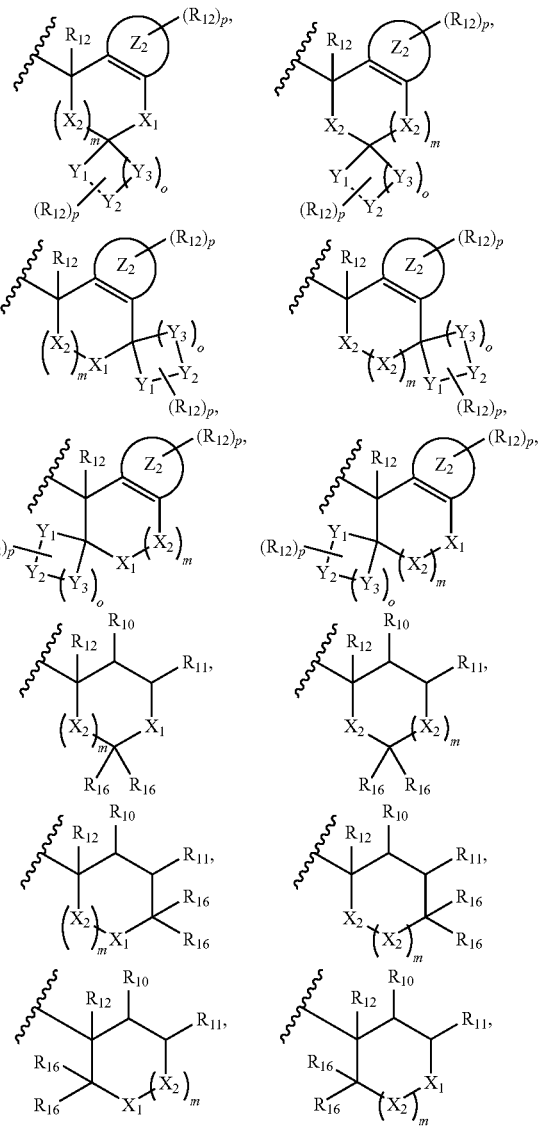

-continued

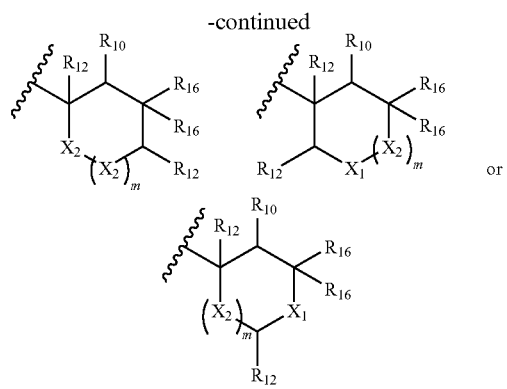

wherein
m, o, $R^{12}$, $X^1$, $X^2$, $Y^1$, $Y^2$ and $Y^3$ are as defined in claim 1;

$Z^2$ is an optionally substituted, partially saturated or fully unsaturated 5-8 membered monocyclic ring, said ring formed of carbon atoms optionally including 1-3 heteroatoms if monocyclic, 1-6 heteroatoms if bicyclic, or 1-9 heteroatoms if tricyclic, said heteroatoms selected from O, N, or S, provided that (a) no more than two of $Y^1$, $Y^2$ and $Y^3$ is O, S or $NR^{12}$ and (b) when o is 0, then each of the $Y^1$ and $Y^2$ is $CR^{12}R^{12}$; and p is 0, 1, 2, 3, 4 or 5;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1-10}$-alkylamino-, $C_{1-10}$-dialkylamino-, $C_{1-10}$-thioalkoxyl, benzyl or phenyl;

$R^{10}$ is H halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic 1-6heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cloalkenyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1-10}$-alkylamino-, $C_{1-10}$-dialkylamino-, $C_{1-10}$-thioalkoxyl, benzyl or phenyl;

$R^{11}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1-10}$-alkylamino-, $C_{1-10}$-dialkylamino-, $C_{1-10}$-thioalkoxyl, benzyl or phenyl;

alternatively, $R^{10}$ and $R^{11}$ taken together with the carbon atoms to which they are attached form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{15}$;

$R^{12}$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pently, cyclopently, hexyl, cyclohexyl, $C_{1-10}$-alkylamino-, $C_{1-10}$-dialkylamino-, $C_{1-10}$-thioalkoxyl, benzyl or phenyl;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$;

$R^{15}$ is H, halo, haloalkyl, CN, OH, $NO_2$, $NH_2$, oxo, acetyl, methyl, methoxyl, ethyl, ethoxyl, propyl, propoxyl, isopropyl, cyclopropyl, butyl, isobutyl, tert-butyl, cyclobutyl, $C_{1-10}$-alkylamino-, $C_{1-10}$-dialkylamino-, $C_{1-10}$-thioalkoxyl, benzyl, phenyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, tert-butyl, cyclobutyl, $C_{1-10}$-alkylamino-, $C_{1-10}$-dialkylamino-, $C_{1-10}$-thioalkoxyl, benzyl or phenyl;

each $R^{16}$, independently, is haloalkyl, methyl, methoxyl, ethyl, ethoxyl, alkoxy-alkyl, alkylamino-alkyl, dialkylamino-alkyl, propyl, propoxyl, isopropyl, isopropoxyl, cyclopropyl, butyl, isobutyl, sec-butyl or tert-butyl;

i is 1; and j is 0.

9. The compound of claim 1, or a pharmaceutically acceptable salt thereof, selected from:

3-(1-acetylpiperidin-2-yl)-5-(1-cyclohexylethyl)-N-((2S,3R)-4-((S)-6-ethyl-2,2-spirocyclopentylchroman-4-ylamino)-3-hydroxy-1-phenylbutan-2-yl)benzamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-fluoro-3-(2-pyridinyl)benzamide;

N-((2 S,3 R)-4-((S)-6-ethyl-2,2-spirocyclobutyl-chroman-4-ylamino)-3-hydroxy-1-phenylbutan-2-yl)benzenesulfonamide;

(R)-3-(benzyloxy)-N-((2S,3R)-4-((S)-6-ethyl-2,2-spirocyclopentyl-chroman-4-ylamino)-3-hydroxy-1-phenylbutan-2-yl)-2,3-dihydro-1H-indene-5-carboxamide;

3-cyclopentyl-N-((2S,3R)-4-((S)-6-ethyl-2,2-spirocyclopentylchroman-4-ylamino)-3-hydroxy-1-phenylbutan-2-yl)-5-(thiophen-2-yl)benzamide;

3-cyclopentyl-N-((2S,3R)-4-((S)-6-ethyl-2,2-cyclopentylchroman-4-ylamino)-3-hydroxy-1-phenylbutan-2-yl)-5-(2-oxopyrrolidin-1-yl)benzamide;

3-(3-cyano-1H-indol-1-yl)-5-cyclopentyl-N-((2S,3R)-4-((S)-6-ethyl-2,2-cyclopentylchroman-4-ylamino)-3-hydroxy-1-phenylbutan-2-yl)benzamide;

3-cyclopentyl-N-((1S,2R)-3-(((4 S)-6-ethyl-2,2-dimethyl-3,4-dihydro-2H-chromen-4-yl)amino)-2-hydroxy-1-(phenylmethyl)propyl)-5-(2-oxo-1-pyrrolidinyl)benzamide;

3-(2-cyano-1H-pyrrol-1-yl)-5-cyclopentyl-N-((1S,2R)-3-(((4 S)-6-ethyl-2,2-dimethyl-3,4-dihydro-2H-chromen-4-yl)amino)-2-hydroxy-1-(phenylmethyl)propyl)benzamide;

N-((1 S,2R)-1-((3-cyanophenyl)methyl)-3-(((4S)-6-ethyl-3,4-dihydrospiro[chromene-2, 1'-cyclobutan]-4-yl)amino)-2-hydroxypropyl)-5-isoxazolecarboxamide;

N-((2S,3R)-4-((S)-6-ethyl-2,2-spirocyclopentylchroman-4-ylamino)-3-hydroxy-1-phenylbutan-2-yl)-5-oxo-3,4,5,6-tetrahydro-2H-benzo[b]oxazocine-10-carboxamide;

N-((2 S,3 R)-4-((S)-6-ethyl-2,2spirocyclobutylchroman-4-ylamino)-3-hydroxy-1-phenylbutan-2-yl)-2-fluoro-3-(2-oxopyrrolidin-1-yl)benzamide;

N-((1S,2R)-3-(((2R,4S)-6-ethyl-3,4,4',5'-tetrahydrospiro[chromene-2,3'-furan]-4-yl)amino)-2-hydroxy-1-(phenylmethyl)propyl)-4-fluoro-3-(2-oxo-1-pyrrolidinyl)benzamide;

N-((1S,2R)-3-(((2R,4S)-6-ethyl-3,4,4',5'-tetrahydrospiro[chromene-2,3'-furan]-4-yl)amino)-2-hydroxy-1-(phenylmethyl)propyl)-2-fluoro-3-(2-oxo-1-pyrrolidinyl)benzamide;

N-((1 S,2R)-1-((3-cyanophenyl)methyl)-3-(((4S)-6-ethyl-3,4-dihydrospiro[chromene-2,1'-cyclobutan]-4-yl)amino)-2-hydroxypropyl)-2-fluoro-3-(2-oxo-1-pyrrolidinyl)benzamide;

N-((1 S,2R)-3-(((1S)-3,3-dimethyl-7-(methyloxy)-4-oxo-1,2,3,4-tetrahydro-1-naphthalenyl)amino)-2-hydroxy-1-(phenylmethyl)propyl)-2-fluoro-3-(2-oxo-1-pyrrolidinyl)benzamide;

N-((1 S,2R)-3-(((1 S)-3,3-dimethyl-7-(methyloxy)-4-oxo-1,2,3,4-tetrahydro-1-naphthalenyl)amino)-2-hydroxy-1-(phenylmethyl)propyl)-3-(1,1-dioxido-1,2-thiazinan-2-yl)-2-fluoro-5-((1-methylethyl)amino)benzamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-1-((1R)-1-phenylethyl)-1H-benzimidazole-6-carboxamide;

4-bromo-N-((1S,2R)-3-(((4'S)-6'-bromo-3',4'-dihydrospiro[cyclobutane-1,2'-pyrano[2,3-b]pyridin]-4'-yl)amino)-2-hydroxy-1-(phenylmethyl)propyl)-1-(2-phenylethyl)-1H-indole-6-carboxamide;

N-((1S,2R)-3-(((4'S)-6'-bromo-3',4'-dihydrospiro[cyclobutane-1,2'-pyrano[2,3-b]pyridin]-4'-yl)amino)-2-hydroxy-1-(phenylmethyl)propyl)-4-(2-cyanophenyl)-1-(2-phenylethyl)-1H-indole-6-carboxamide;

N-((1S,2R)-3-(((4S)-6-ethyl-3,4-dihydrospiro[chromene-2,1'-cyclobutan]-4-yOamino)-2-hydroxy-1-(phenylmethyl)propyl) benzenesulfonamide;

N-((1S,2R)-3-(((4S)-6-bromo-3,4-dihydrospiro[chromene-2,1'-cyclobutan]-4-yl)amino)-2-hydroxy-1-(phenylmethyl)propyl)-1,8-naphthyridine-2-carboxamide;

5-bromo-2-butyl-N-((1S,2R)-3-(((4S)-6-ethyl-3,4-dihydrospiro[chromene-2,1'-cyclopentan]-4-yl)amino)-2-hydroxy-1-(phenylmethyl) propyl)-1,3-benzoxazole-7-carboxamide;

5-((1,1-dimethylethyl)sulfonyl)-N-((1S,2R)-3-(((4S)-6-ethyl-3,4-dihydrospiro[chromene-2,1'-cyclobutan]-4-yl)amino)-2-hydroxy-1-(phenylmethyl)propyl)-2-thiophenecarboxamide;

N-((1S,2R)-3-(((4S)-6-ethyl-3,4-dihydrospiro[chromene-2,1'-cyclobutan]-4-yl)amino)-2-hydroxy-1-(phenylmethyl)propyl)-2-(2-(ethyloxy)phenyl)-4-quinolinecarboxamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-fluorobenzamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-pyridinecarboxamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1((4-fluorophenyl)methyl)-2-hydroxypropyl)-3-methyl-2-pyridinecarboxamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-5-isoxazolecarboxamide;

'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3-fluoro-2-pyridinecarboxamide; and 'N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(((4-fluorophenyl)methyl)-2-hydroxypropyl)-2-((trifluoromethyl)oxy)benzamide.

10. A pharmaceutical composition comprising a pharmaceutically acceptable carrier and a compound according to claim 1.

11. A method of making a compound of claim 1, the method comprising the step of reacting a compound 20

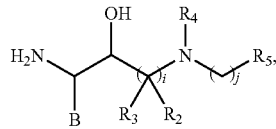

wherein i, j, A, B, $R^3$, $R^4$ and $R^5$ are as defined in claim 1, with a compound having the structure $R^1$—W—X, wherein $R^1$ and W are as defined in claim 1 and X is a leaving group, to make a compound of claim 1.

* * * * *